United States Patent
Tajima

(10) Patent No.: US 8,133,454 B2
(45) Date of Patent: Mar. 13, 2012

(54) BIOLOGICAL MATERIAL FIXED REGION ENCLOSING TIP, BIOLOGICAL MATERIAL FIXED REGION TREATMENT APPARATUS, AND TREATMENT METHOD THEREOF

(75) Inventor: Hideji Tajima, Chiba (JP)

(73) Assignee: Universal Bio Research Co., Ltd., Matsudo-Shi, Chiba (JP)

( * ) Notice: Subject to any disclaimer, the term of this patent is extended or adjusted under 35 U.S.C. 154(b) by 207 days.

(21) Appl. No.: 11/792,783

(22) PCT Filed: Dec. 12, 2005

(86) PCT No.: PCT/JP2005/022776
§ 371 (c)(1),
(2), (4) Date: May 21, 2008

(87) PCT Pub. No.: WO2006/062236
PCT Pub. Date: Jun. 15, 2006

(65) Prior Publication Data
US 2008/0257073 A1 Oct. 23, 2008

(30) Foreign Application Priority Data
Dec. 10, 2004 (JP) .................................. 2004-359202

(51) Int. Cl.
*B01L 3/00* (2006.01)
(52) U.S. Cl. ....... 422/501; 422/502; 422/503; 422/68.1; 422/50; 436/54; 436/180; 436/178; 436/43; 435/6; 435/174; 435/287.2; 435/11
(58) Field of Classification Search ........... 435/6, 287.2; 422/62, 64, 100
See application file for complete search history.

(56) References Cited

U.S. PATENT DOCUMENTS
5,403,745 A 4/1995 Ollington
(Continued)

FOREIGN PATENT DOCUMENTS
EP 1464700 10/2004
(Continued)

OTHER PUBLICATIONS
International Searching Authority "International Search Report," Mar. 7, 2006, International Application No. PCT/JP2005/022776, Japanese Patent Office, 4 pages.
(Continued)

*Primary Examiner* — Sally Sakelaris
(74) *Attorney, Agent, or Firm* — Haynes and Boone, LLP

(57) ABSTRACT

A biological material fixed region enclosing tip, a biological material fixed region treatment apparatus, and a treatment method thereof. An object is to enable processing to be performed while a fixing region is enclosed in an immovable state with respect to the tip form vessel, and to execute processing of high reliability with a simple apparatus. The biological material fixed region enclosing tip comprises: a tip form vessel having an installation opening part that is installable to a nozzle that performs suction and discharge of gas, and an opening through which inflow and outflow of fluid is possible by means of the suction and discharge of gas; a fixing region provided in the tip form vessel, in which a predetermined biological material is fixed or fixable in a plurality of different positions that are determined beforehand that are distinguishable from the exterior; and an enclosing section that encloses the fixing region within the tip form vessel such that the fixing region is able to make contact in an immovable state with the fluid that has flown into the tip form vessel from the opening.

9 Claims, 12 Drawing Sheets

U.S. PATENT DOCUMENTS

| | | | |
|---|---|---|---|
| 5,478,526 | A | 12/1995 | Sakai et al. |
| 5,895,631 | A | 4/1999 | Tajima |
| 6,096,554 | A | 8/2000 | Tajima |
| 6,312,886 | B1 | 11/2001 | Lee et al. |
| 6,436,355 | B1 | 8/2002 | Lee et al. |
| 6,509,193 | B1 | 1/2003 | Tajima |
| D560,815 | S | 1/2008 | Tajima |
| D561,347 | S | 2/2008 | Tajima |
| D561,906 | S | 2/2008 | Tajima |
| D565,192 | S | 3/2008 | Tajima |
| D569,989 | S | 5/2008 | Tajima |
| 2001/0019826 | A1 | 9/2001 | Ammann |
| 2002/0090729 | A1 | 7/2002 | Neeper et al. |
| 2002/0110817 | A1 | 8/2002 | Tajima |
| 2003/0064386 | A1* | 4/2003 | Karaki et al. ............... 435/6 |
| 2004/0166504 | A1 | 8/2004 | Rossier et al. |
| 2005/0124058 | A1 | 6/2005 | Tajima |
| 2008/0193995 | A1 | 8/2008 | Tajima |
| 2009/0298160 | A1 | 12/2009 | Tajima et al. |

FOREIGN PATENT DOCUMENTS

| | | |
|---|---|---|
| EP | 1589332 | 10/2005 |
| JP | 03-181853 | 8/1991 |
| JP | 08-062225 | 3/1996 |
| JP | 09-262084 | 10/1997 |
| JP | 10-117764 | 5/1998 |
| JP | 10-323177 | 12/1998 |
| JP | 2000-241436 | 9/2000 |
| JP | 2000-346842 | 12/2000 |
| JP | 2001-002695 | 1/2001 |
| JP | 2001-074756 | 3/2001 |
| JP | 2002-102681 | 4/2002 |
| JP | 2002-189033 | 7/2002 |
| JP | 2002-191351 | 7/2002 |
| JP | 2003-107083 | 4/2003 |
| JP | 2003-339374 | 12/2003 |
| JP | 2004-033907 | 2/2004 |
| JP | 2004-061397 | 2/2004 |
| JP | 2005-030906 | 2/2005 |
| JP | 2005-278437 | 10/2005 |
| WO | WO 91/17441 | 11/1991 |
| WO | WO 97/26539 | 7/1997 |
| WO | WO 99/57561 | 11/1999 |
| WO | WO 00/67893 | 11/2000 |
| WO | WO 03/004160 | 1/2003 |
| WO | WO 2004/068125 | 8/2004 |
| WO | WO 2006/073170 | 7/2006 |

OTHER PUBLICATIONS

English Translation of Response to Written Opinion mailed Mar. 27, 2006 in priority International Application No. PCT/JP2005/022776, Response filed Oct. 10, 2006, 18 pages.
U.S. Appl. No. 11/664,980, filed Jul. 1, 2009, Hideji Tajima et al.
U.S. Appl. No. 29/277,775, filed Mar. 9, 2007, Hideji Tajima.
U.S. Appl. No. 29/277,777, filed Mar. 9, 2007, Hideji Tajima.
U.S. Appl. No. 29/277,778, filed Mar. 9, 2007, Hideji Tajima.
U.S. Appl. No. 29/277,779, filed Mar. 9, 2007, Hideji Tajima.
U.S. Appl. No. 29/277,780, filed Mar. 9, 2007, Hideji Tajima.
U.S. Appl. No. 11/792,835, filed Jun. 8, 2007, Hideji Tajima.
U.S. Appl. No. 11/794,828, filed Dec. 10, 2009, Hideji Tajima.
U.S. Appl. No. 10/501,670, filed Jan. 18, 2005, Hideji Tajima.
Supplemental European Search Report, issued by the European Patent Office, dated Apr. 27, 2011, in Application No. EP 05814454.

* cited by examiner

BIOLOGICAL MATERIAL FIXED REGION ENCLOSING TIP, BIOLOGICAL MATERIAL FIXED REGION TREATMENT APPARATUS, AND TREATMENT METHOD THEREOF

CROSS REFERENCE

This application is a United States national phase application of co-pending international patent application number PCT/JP2005/022776, filed Dec. 12, 2005, which claims priority to Japanese patent application number 2004-359202, filed Dec. 10, 2004, the disclosures of which are incorporated herein by reference.

TECHNICAL FIELD

The present invention relates to a biological material fixed region enclosing tip, a biological material fixed region treatment apparatus, and a method thereof.

BACKGROUND ART

Conventionally, in a case where a series of reaction processes using a plurality of reagents and materials is performed on a target material, which becomes the subject of examination, for example, the target material is stored in a test tube by bonding to a microcarrier, such as a bead. Thereafter, a variety of reagents, or the like, are injected into the test tube, the carrier is separated by some method, the carrier is moved to another vessel, and other reagents, or the like, are further injected, and processes such as heating are performed. For example, in a case where the carrier is a magnetic body, separation is performed by means of a magnetic field by attachment onto the inner wall of the test tube.

Furthermore, in regard to a process that performs examination of a target material by using a plane form carrier, such as a slide, fixed with, for example, a variety of oligonucleotides, the base sequence structure of the target material is examined by performing a series of reaction processes that, moves the carrier itself into a suspension in which the labeled target material is suspended, dispenses a variety of reagents into the carrier itself, moves the carrier itself into a cleaning solution, and moves the carrier to a measurement position of a measuring device in order to perform measurement of the emitted light.

In order to perform these processes, the separation of the carrier itself, and the transport of the carrier itself is necessary, and consequently, there is a problem in that there is concern in the processes being complex and time-consuming. Particularly, in regard to a case where these carriers themselves are transported, a large burden is placed on the user in a case where it is performed manually, and furthermore, there is also concern regarding cross-contamination. Moreover, a large scale device is necessary in a case where transport of the carrier itself is performed by means of a machine. Furthermore, in a case where separation of a non-magnetic carrier is performed, it is necessary to separate by means of the size and specific gravity of the carrier, and there is a problem in the process being complex and time-consuming.

On the other hand, there is a method in which a test tube or a plane form carrier is not used, in which the reaction process is performed using a pipette device comprising; a pipette tip provided with a liquid passage, in which passage of a liquid is possible, a nozzle to which the pipette tip is installed, a magnetic device that exerts a magnetic field to the liquid passage of the pipette tip, and a suction and discharge mechanism that suctions and discharges liquid within the pipette tip.

According to this method, as a result of suctioning a suspension in which a plurality of magnetic particles, in which various materials are retained on the surface, are suspended, and exerting a magnetic field at the time of suctioning, the magnetic particles can be efficiently suctioned into the liquid passage of the pipette tip, and separation, or the like, can be performed.

In the case of using the apparatus, since the magnetic particles are able to pass through the liquid passage, in order to retain the magnetic particles within the pipette tip, attachment onto the inner wall by applying a magnetic field is necessary. Consequently, in order to perform processing, there is a need to combine the suction and discharge control, attachment control by means of a magnetic field, and movement control of the pipette tip. Furthermore in regard to a case where the carrier is a non-magnetic particle, there is a problem in that separation can not be performed by the device (Patent Documents 1 to 3).

[Patent Document 1] Japanese Patent Publication No. 3115501
[Patent Document 2] International Patent Publication No. WO96/29602
[Patent Document 3] International Patent Publication No. WO97/44671

DISCLOSURE OF INVENTION

Problems to be Solved by the Invention

Consequently, a first object of the present invention is in providing: a biological material fixed region enclosing tip, wherein by making it possible to perform processing on a fixing region in which the various materials are fixed or are fixable, while it is enclosed and retained within a tip form vessel, attachment control and suction control for storing and retaining the fixing region in the tip form vessel is made unnecessary, complex reaction processes are simplified, and processing is made to be easily executed as a result of a small-scale device configuration; a biological material fixed region treatment apparatus; and the method thereof.

A second object is in providing: a biological material fixed region enclosing tip, wherein by making it possible to perform the enclosing and the removal of a fixing region in which the various materials are fixed or are fixable, through a separate route to the route that performs suction and discharge of fluid or a material that is present within the fluid, then a process in which the fixing region and the fluid is divided is made unnecessary, complex reaction processes are simplified, and processing is made to be easily executed as a result of a small-scale device configuration; a biological material fixed region treatment apparatus; and the method thereof.

A third object is in providing: a biological material fixed region enclosing tip, wherein processing can be made efficient, and the reliability of processing and certainty of processing can be increased by, in regard to a fixing region in which the various materials are fixed or are fixable, making it able to be easily enclosed by the tip form vessel that stores the same, and making processing with respect to the fixing region easily executed; a biological material fixed region treatment apparatus; and the method thereof.

A fourth object is in providing: a biological material fixed region enclosing tip, in which by suitably determining the shape and the size of the fixing region without being restricted to a magnetic body material, separation can be made easy, and therefore the breadth of selections with respect to the material, increases, and the optimal material for processing can be selected; a biological material fixed region treatment apparatus; and the method thereof.

A fifth object is in providing: a biological material fixed region enclosing tip, wherein automation in regard to consistent processing is made easy; a biological material fixed region treatment apparatus; and the method thereof.

Means for Solving the Problem

A first aspect of the invention is a biological material fixed region enclosing tip comprising: a tip form vessel having an installation opening part that is installable to a nozzle that performs suction and discharge of gas, and an opening through which inflow and outflow of fluid is possible by means of the suction and discharge of gas; a fixing region provided in the tip form vessel, in which a predetermined biological material is fixed or fixable in a plurality of different positions that are determined beforehand that are distinguishable from the exterior; and an enclosing section that encloses the fixing region within the tip form vessel such that the fixing region is able to make contact in an immovable state with the fluid that has flown into the tip form vessel from the opening.

Here, the "predetermined biological material" is a biopolymer, for example, genetic material such as nucleic acids, proteins, sugars, sugar chains, or peptides, or chemical materials including low molecular weight compounds, and the biological material is used for detecting the bonding of a receptor biological material that possesses bondability to the biological material as a ligand, capturing, separating, extraction, and the like. As the receptor, genetic material such as nucleic acids, proteins, sugar chains, peptides, or the like, that respectively possess bondability to genetic material such as nucleic acids, proteins, sugar chains, peptides, or the like, are appropriate. Furthermore, as the biological material, or a replacement for the biological material, the organism itself, such as cells, viruses, and plasmids, can be used. "Fixed", for example, includes cases of physical adsorption or electrical interaction in addition to the cases of covalent bonding and chemical adsorption. Furthermore, the predetermined chemical material is fixed to the fixing region; chemically, by physical adsorption, by a specific reaction with a binding material provided fixed in an appropriate area, or by another method. Moreover, the reaction ability or the bonding ability with the biological material may be increased by forming the fixing region with a porous material, a corrugated material, or a fibrous material. In order to perform fixing, a functional group is expressed or generated in the fixing region. Consequently, by hydrolyzing the peptide bonds possessed by, for example, silk, or the like, which comprises "polyamide type polymers", totally aromatic polyamides such as nylon (3-nylon, 6-nylon, 6,6-nylon, 6,10-nylon, 7-nylon, 12-nylon, or the like) and PPTA (polyparaphenylene terephthalamide), or heterocycle-containing aromatic polymers, the functional groups used for fixing the biological material is expressed or generated. Examples of functional groups that are bondable with the biological material include carboxyl groups —COOH, amino groups —$NH_2$, and the derivatives thereof. Here, the pore diameter suitable for fixing the biological material is, for example, several micrometers or less.

The "fixing region" is a region where one type of more of the biological materials are fixed or are fixable, and is enclosed in the tip form vessel by the enclosing section. Examples of the fixing region include for example regions which are formed on the internal surface of the vessel, and on plane form carriers of plate-shaped carriers and the like having various sizes. "Fixing region" is preferably a plurality of different positions that are determined beforehand that are distinguishable from the exterior. These may be planar regions that can be specified by a two dimensional position coordinate, and are not only a flat surface but may also be a curved surface.

In the case where one or more types of biological materials is fixed to the fixing region, the predetermined types of biological materials can be arranged so as to become a predetermined relationship to the predetermined positions of the fixing region. In that case, as a result of a solution containing a biological material that is labeled by a labeling material comprising a luminescent material, such as a fluorescent material in which there is the possibility of bonding with these biological materials, making contact with the fixing region, the presence of bonding with these biological materials is measured by measuring the luminescence at each position, and as a result of this, the structure, the characteristics, and the presence of the target biological material can be analyzed. Furthermore, by fixing one or more types of biological materials to the fixing region, the target biological material can be separated and extracted. "Contact in an immovable state" means that the whole fixing region is able to make contact with the fluid without being moved relative to the tip form vessel by the fluid flowing inside the tip form vessel.

Examples of the "enclosing section" include, for example in the case where the fixing region is provided on the internal surface of the vessel: a lid member provided on the tip form vessel, for covering the opening part from the outside of the tip form vessel for enclosing the fixing region inside the tip form vessel, by covering the distribution opening part for distribution of the biological material to the fixing region; an attachment member for attaching the plane form carrier serving as the fixing region, to the tip form vessel; or a protrusion member with the plane form carrier attached as a fixing region that forms the tip form member.

The "tip form vessel" is a vessel provided with an installation opening part and an opening. The installation opening part is provided on the upper end, the opening is provided on the lower end, and it is preferable for the opening to be narrower than the installation opening part, and to be provided on the end of the narrow tube, which is insertable into various vessels. In this case it is preferable to provide a fixing region forming section that forms the fixing region, between the narrow tube and the installation opening part, to communicate between these. In regard to the fixing region forming section, it is preferable for it to have a wide tube that is formed wider than the narrow tube. In regard to the wide tube and the narrow tube, this is not limited to a case having a typical tube shape such as with a wide diameter tube and a narrow diameter tube. For example, instead of a wide diameter tube, this may be a vessel that has a thin rectangular box shape, having the installation opening to the nozzle on an upper end portion, and having a shape to communicate the thin diameter portion with the lower end. In regard to the material of the tip form vessel, it is preferable for the portion that encloses the fixing region to be translucent in order to enable optical measurements to be performed. If the fixing region is provided in a portion other than the narrow tube, inside the tip form vessel, then the fixing region can be widened. Examples of the material of the tip form vessel include resins such as polyethylene, polypropylene, polystyrene, and acrylic, glass, metals, and metal compounds. In regard to the size, for example, it is a size in which several microliters to several hundred microliters of liquid is storable in the tip form vessel.

A second aspect of the invention is a biological material fixed region enclosing tip wherein the fixing region is provided on the plane form carrier which is detachably attached inside the tip form member, and the tip form member has a carrier insertion opening insertable by the plane form carrier, and the enclosing section is attached inside the tip form member, so that fluid that has flown in from the opening inside the tip form member is able to contact with the plane form carrier.

Here the "carrier", with respect to the tip form vessel, is a solid body having a size capable of insertion or removal from the carrier insertion opening. Normally this cannot pass through the opening. Inside the tip form vessel, the minimum amount of liquid that is handled is a volume of for example several microliters to several hundred microliters, and it is necessary for the whole surface of the carrier to be able to contact with the liquid. Therefore, it is appropriate if the volume of the space surrounded by the surface of the carrier inserted into the fixing region forming section, and the internal surface of the vessel, has a volume corresponding to the minimum amount. The carrier itself may be translucent, or may be non translucent. In the case where this is non translucent, both surfaces can be used as the fixing region. Furthermore, the carrier is preferably stored in the fixing region forming section provided between the installation opening part and the narrow tube.

Consequently, the size of the opening of the tip form vessel for simplifying the suction and the discharge of the liquid quantity, and the size of the carrier for enabling it to pass through the carrier insertion opening part is considered. Here the "plate-shaped carrier" may be a carrier where a plurality of different positions that are determined beforehand that are distinguishable from the exterior, can be specified by a two dimensional position coordinate. It may be a carrier having not only a flat surface but also one having at least one curved surface. Even if this is a plate-shaped carrier, a thin film form carrier, or a block form carrier, it is sufficient if a plane surface or a curved surface is formed that can be specified by at least one two dimensional position coordinate.

The carrier is a solid body that is, for example, fixed such that it is arranged with a spacing, or is fixable, such that one or more types of the predetermined types of biological materials become a predetermined relationship to the predetermined positions. In that case, as a result of a solution containing a biological material that is labeled by a labeling material comprising a luminescent material, such as a fluorescent material in which there is the possibility of bonding with these biological materials, making contact with the carrier, the presence of bonding with these biological materials is measured by measuring the luminescence at each position, and as a result of this, the structure, the characteristics, and the presence of the target biological material can be analyzed.

Since the plane form carrier is insertable to inside the tip form vessel from the carrier insertion opening, fixing of the biological material can be performed on the outside of the tip form vessel. Consequently, the fixing process for the biological material is easy. The carrier insertion opening may be used in conjunction with the installation opening part, or may also be provided separate to the installation opening part. In the case where this is provided separate to the installation opening part, then as the enclosing section, a lid member for closing the carrier insertion opening is necessary.

As the tip form vessel, there is one having translucence such that light emitted by the plane form carrier can be measured. Furthermore, for example, preferably this has a portion formed in an approximate quadratic prism shape that matches with the size and shape of the plane form carrier.

The carrier is, for example, a porous body or a solid body in which a functional group that is able to bond to the biological material is generated or expressed at the surface, or a combination of both. For example, it is formed by a fibrous material such as rubber, silicone, cellulose or nylon, a resin, glass, or a metal.

Since "in the enclosing section fluid that has flown in from the opening inside the tip form member is able to contact with the plane form carrier", it is necessary to attach by providing the enclosing section on the tip form vessel inside, and so that the face fixed with the biological material is not a tight fit with the inner wall of the tip form member. The enclosing portion may be: one where the tip form vessel is provided modified or processed; one where the tip form vessel is provided separately; or one where a separately provided the tip form vessel and one where processing has been performed on the walls and the like of the tip form vessel, are assembled together. As one where the tip form vessel is used as is, there is one where a protrusion portion is provided that protrudes towards the center of the tip form vessel. As the one where the tip form vessel is provided separately, there is for example a lid member that closes the opening provided on the tip form vessel in order to enclose the fixing region. The screws, adhesive, weld metal for attaching the carrier or the lid member to the tip form member, are also included with the lid member.

The "lid member" is preferably a member of a plane form of for example a thin film or a thin plate. By forming an electrically conductive thin film as described later, then this may also be heated and cooled.

A third aspect of the invention is a biological material fixed region enclosing tip wherein the tip form vessel has a distribution opening that is capable of distributing the biological material with respect to the fixing region, and the enclosing section has a lid member that covers the distribution opening, so that fluid that has flown in from the opening can contact with the fixing region.

A fourth aspect of the invention is a biological material fixed region enclosing tip wherein the fixing region is provided on an internal surface of the tip form vessel, and the distribution opening is provided on a wall facing the internal surface.

Here for the tip form vessel, for example this has a portion formed in an approximate quadratic prism shape, and the fixing region is provided so as to occupy a predetermined internal surface of one side face of the quadratic prism of the tip form vessel, and the distribution opening has a wall face along the predetermined internal surface, which is provided so that the fixing region can be reached by a tip of a dispensing unit or the like from the outside that has passed through the other side face.

A fifth aspect of the invention is a biological material fixed region enclosing tip wherein the volume of a space in which liquid is storable within the tip form vessel with the fixing region enclosed is several microliters to several hundred microliters.

By setting the volume of the tip form vessel in this manner, then even if liquid of a small amount, for example liquid of a volume of several microliters to several hundred microliters, is drawn in to the tip form vessel, the liquid can uniformly or evenly contact with the surface of the carrier. This small amount, in conventional biological analysis, in particular DNA analysis, is an amount of material that is easily extracted from an organism and handled. Furthermore, as the tip form vessel, a large tube that communicates with the carrier storing section may be provided in addition to the carrier storing section that stores the carrier. For example by making this several times to several ten times the volume of the carrier storing section, then various liquid amounts can be handled.

A sixth aspect of the invention is a biological material fixed region enclosing tip wherein the fixing region is formed on one face of the plane form carrier, and on the tip form vessel there is provided a fluid contact opening part for enabling contact between the fixing region of the plane form carrier and fluid that has been introduced from the opening, and the enclosing section has an attaching member that attaches the plane form carrier from outside of the tip form carrier so that the fixing region of the plane form carrier is positioned in the contact opening part.

Here the attaching member is a member for attaching the plane form carrier to the tip form vessel, and for example is an attachment device such as adhesive, screws, or an engaging member. The plane form carrier or the plane form member of the thin film carrier or the like, may be such as to form an electroconductive member having a predetermined electrical resistance value as described later.

A seventh aspect of the invention is a biological material fixed region enclosing tip wherein the entire wall of the tip form vessel, or a portion thereof, is formed by an electroconductive member that has a predetermined electrical resistance value.

Here, by providing the electroconductive member to the tip form vessel, heat generation can be induced by making a terminal that is connected to an electrical circuit provided on the exterior come into contact with the electroconductive member, and by flowing an electrical current through the electroconductive member, which has a predetermined resistance value. The resistance value is controlled by a control section mentioned below, based on the processing contents.

Moreover, as the "predetermined electrical resistance value", it is a value in which the heat generation that is necessary for the electroconductive member to achieve a temperature according to the object can be performed by flowing a fixed electrical current within the electroconductive member. For example, in terms of the surface resistance value, it is, for example, several hundred ohms to several ohms per unit area, and furthermore, the resistance value at which induction heating is made possible is, for example, several ohm cm or more. As the conductive thin film, for example, there is a case where it comprises a single type of material that has a predetermined electrical resistance, or there is a case where two or more types of materials that have different resistance values are joined, adhered, deposited, fused, welded, bonded, attached, or pasted. In the former case, the temperature depends on the magnitude of the electrical current value, which is the electromagnetic signal, and in the latter case, as a result of the Peltier effect, the temperature depends not only on the electrical current value but also the orientation of the current, and not only heating, but cooling also becomes possible.

Examples of the "electroconductive member" include metals, metallic compounds such as metal oxides, conductive materials such as alloys, semiconductors, metalloids, and conductive resins, a combination of these conductive materials with non-conductive materials such as ceramics, glass, and synthetic resins, or it may be a combination between conductive materials. For example, there are cases of aluminum, aluminum oxide, tin oxide, iron, an iron alloy, a nichrome alloy, and a member formed by two types of different conductive materials that have been bonded by means of bonding, welding, or joining. By flowing an electrical current to these members, or in the case of iron or an iron alloy, by applying a temporally oscillating magnetic field, these members can be inductively heated. In a case where two types of conductive materials have been joined, heating and cooling can be performed by means of the orientation of the electrical current.

Examples of the shape of the electroconductive member include a linear form, a thin-film form, a foil form, a film form, a thin plate form, a plate form, a long and narrow shape, and a layer form. The electroconductive member may be bonded, welded or deposited on a non-conductive member in order to reinforce the electroconductive member. The electroconductive member is controlled to a predetermined temperature by means of the "electromagnetic signal" (an electrical signal or a magnetic signal). Thermodynamic signals resulting from the application of heat or cold air are excluded from the electromagnetic signal.

In regard to the wall, the inner wall face thereof faces into the tip form vessel, the outer wall face thereof is on the exterior of the tip form vessel, and it is a tip form vessel wherein the interval between the inner and outer wall faces is integrally formed. That is to say, the portion of the wall that is sandwiched by the inner wall face and the outer wall face of the tip form vessel is, for example, a metal, a resin, or the like, or it is formed as a wall in a solid state in which these have been bonded such that they are not freely divided. Consequently, as the electroconductive member that has been formed as the entire wall or a portion of the wall, in a case where this has an electroconductive member that is freely separable from the wall, then for example, electroconductive members that simply only make contact with the wall, electroconductive members that are freely detachably installed to the wall by means of a screw, or the like, electroconductive members that are freely detachably provided with respect to a separate member that is installed to the wall by welding, or the like, and electroconductive members that are completely separated from the wall, are able to be divided, and are therefore excluded. Consequently, if the electroconductive member is provided such that the wall of the tip form vessel becomes approximately the thickness demanded as the wall of the tip form vessel, then the size of the tip form vessel and the scale of the entire device is controlled, and it can be handled without an awareness of the presence of the heating device.

An eighth aspect of the invention is a biological material fixed region treatment apparatus comprising: a nozzle head that has one or a plurality of consecutive nozzles that perform suction and discharge of gas; a suction and discharge mechanism that performs suction and discharge of gas via the nozzles; one or two or more biological material fixed region enclosing tips that are installed or are installable to the nozzles, in which a fixing region, to which biological material is fixable or is fixed, is enclosed; a stage to which a liquid storage section group, in which a variety of liquids are stored or are storable, is provided; a movement device that relatively moves the nozzle head with respect to the liquid storage section group; and a control section that controls the suction and discharge operations comprising the amount, the speed, the frequency, the time, or the position of the suction and discharge of the nozzles based on; the structure of the biological material fixed region enclosing tip, the material conditions comprising the type of biological material that is fixed to the fixing region or is present within the fluid, the concentration, the amount of liquid, and the coordinate position containing the storage position of the liquid, and the processing contents.

Here the "biological material fixed region enclosing tip" comprises, for example; a tip form vessel that has an installation opening part that is installed to the nozzle, and an opening through which inflow and outflow of fluid is possible by means of the suction and discharge of the gas, a fixing region in which a predetermined biological material is fixed or is fixable at a plurality of different positions determined beforehand that are identifiable from the exterior, that is provided in the tip form vessel, and an enclosing section that encloses the fixing region within the tip form vessel such that the fixing region is able to make contact in an immovable state with the fluid that has flown into the tip form vessel from the opening.

Moreover, since there are "one or two or more biological material fixed region enclosing tips that are installed or are installable to the nozzles", the biological material fixed region enclosing tips are arranged in the middle of the vessel group, and the nozzles can be inserted into the installation opening part and automatically installed and used. Furthermore, by providing a mechanism for removing the biological material fixed region enclosing tips from the nozzles in which they are installed, then consistent processing including processing from installation of the biological material fixed region enclosing tips to their removal removing can be performed.

Here, the "processing contents" are, for example, reaction, cleaning, transporting, dispensing, separating, extracting, heating, cooling, clarifying, measuring, mixing, deviating, elution, stirring, or the like, or a series of these processes that are combined according to a predetermined order or a predetermined time schedule according to a processing objective while including overlaps. "Time" includes the duration time or the timing of suction and discharge. By setting the duration time or the timing, intermittent, continuous or periodic setting of the suction and discharge is made possible.

In the case of "reaction" processing, for example, according to the material conditions, in regard to the vessel position in which the corresponding reagent is stored, a control in which; the suction and discharge that is determined by the conditions is performed at a predetermined speed, and suction and discharge is repeated at a liquid quantity of, for example, 80 percent of the capacity of the carrier enclosing region of the tip form vessel, is performed. In regard to the frequency of the suction and discharge thereof, the determined control is performed according to the material conditions. In the case of "cleaning" processing, for example, according to the material conditions, in regard to the vessel position in which the cleaning solution is stored, a control in which; the suction and discharge that is determined according to the process is performed at a predetermined speed, and suction and discharge is repeated a predetermined number of times, is performed. In the same manner, control of the suction and discharge according to the process is performed. In regard to the "speed", for example, since in a case where the handled material is DNA, the size thereof is small compared to proteins, it is necessary to increase the speed in order to increase the encounterability between DNA. Furthermore, the speed differs depending on the contents of processing, and in the case of cleaning and stirring, the speed of the suction and discharge thereof is low compared to a case where the reaction process is performed.

The "structure of the biological material fixed region enclosing tip" also includes the shape of the tip, the position of the enclosed fixed region, the shape and the characteristics of the carrier, the shape of the enclosing section, or the like. Determining the action of the suction and discharge according to the "type of the biological material" means that, for example, in a case where it is generally smaller than the size of proteins, such as in the manner of genetic material such as DNA, it is easier to handle if the handled liquid quantity is small, and the speed is fast. This is because the smaller the size, the encounterability generally becomes low.

A ninth aspect of the invention is a biological material fixed region treatment apparatus further comprising a light reception device that receives light from the fixing region stored within the tip form vessel.

In regard to the light reception by means of the light reception device, there is a case where it is collectively performed with respect to a plurality of biological material fixed region enclosing tips that are installed to a nozzle head that has a plurality of consecutive nozzles, and there is a case where light reception is serially performed for each of the biological material fixed region enclosing tips by means of the light reception device. In the latter case, it is performed by using a movement device that relatively moves between the light reception device and the vessel while relatively transporting the tip or the light reception device serially one at a time. In that case, since the measurement is performed by shifting the time, some kinds of reagents, for example, the PCR reaction solution in the previous process of PCR, in a case where extraction of DNA is performed, or a substrate solution to be injected in the case of chemiluminescence, need be dispensed immediately before reaction or a fixed time before reaction. Consequently, dispensing is not performed simultaneously, and it is preferable for dispensing to be performed by temporally shifting one at a time and providing a time difference. In a case where fluorescence is measured, a luminescent device that irradiates a predetermined excitation light into the vessel is further provided.

A tenth aspect of the invention is a biological material fixed region treatment apparatus wherein a space in which liquid is storable within the tip form vessel, is several microliters to several hundred microliters.

Consequently, in regard to the liquid storage section provided on the exterior of the biological material fixed region enclosing tip, the several microliters to several hundred microliters of liquid must be storable such that it is able to be suctioned into the tip through the opening.

An eleventh aspect of the invention is a biological material fixed region treatment apparatus wherein a temperature raising and lowering body that raises and lowers the temperature as a result of a signal from the exterior is provided in the vicinity of, making contact with, or able to be in the vicinity of or making contact with, the outside of the tip form vessel of the biological material fixed region enclosing tip.

Here, the "temperature raising and lowering body" refers to a member or a device that is able to raise or lower the temperature thereof according to a signal from the exterior. The "signal" is, in a case where the temperature raising and lowering body is an electroconductive member, an electromagnetic signal, that is to say, a signal resulting from electricity or magnetism. It is also possible to detect the temperature resulting from the temperature raising and lowering body and generate the signal based on the temperature.

It is preferable for the temperature raising and lowering body to be relatively movably provided with respect to the biological material fixed region enclosing tip. Furthermore, in this case, the control section, in addition to control of the suction and discharge, consequently controls the temperature control based on the processing contents.

A twelfth aspect of the invention is a biological material fixed region treatment apparatus wherein the nozzle head has a collective nozzle head in which a plurality of consecutive nozzles are arranged along the column direction and an individual nozzle head that has at least one nozzle, the suction and discharge mechanism has a collective suction and discharge mechanism that simultaneously performs suction and discharge of gas with respect to the plurality of consecutive nozzles of the collective nozzle head, and an individual suction and discharge mechanism that individually performs suction and discharge of gas with respect to each nozzle of the individual nozzle head, and the movement device has, a nozzle head movement device that relatively moves the collective nozzle head and the individual nozzle head in the row direction with respect to the liquid storage section group, and a transporting route that includes a column transporting route that is on the movement route of the collective nozzle head and along the column direction and a row transporting route that is on the movement route of the individual nozzle head and along the row direction, and has a queued route transporting device that transports a transport storage section, in which tips that have been detached from the collective nozzle head or liquid that has been discharged from the collective nozzle head are respectively storable, along the transporting route.

Here, there is no need for the "column direction" and "row direction" to necessarily be orthogonal such as in an X direction (horizontal direction) and a Y direction (vertical direction), and a case where they are oblique is acceptable. The collective nozzle head and the individual nozzle head may be individually movable. Furthermore, if the queued route transporting device has a row transporting route and a column transporting route on the movement route of the nozzle head, for example, it may be a case where it has a closed transporting route, such as a square shape or a polygonal shape, or it may be a case where it has an open transporting route. The "transport storage section" is a portion that stores the tip or the liquid in the transporting device, and it is preferable if, at the very lest, it has the same number of transport storage sections as the number of nozzles of the collective nozzle head.

A thirteenth aspect of the invention is a biological material fixed region treatment apparatus wherein the nozzle head has a plurality of consecutive collective nozzles and one individual nozzle arranged along the column direction, the suction and discharge mechanism simultaneously performs suction and discharge of gas with respect to the collective nozzles and the individual nozzle of the nozzle head, and the movement device has, a nozzle head movement device that relatively moves the nozzle head along the row direction with respect to a stage that has the liquid storage section group, and a transporting route that includes a column transporting route that is on the movement route of the collective nozzles and along the column direction and a row transporting route that is on the movement route of the individual nozzle and along the row direction, and has a queued route transporting device that transports a transport storage section, in which tip form vessels that have been detached from the collective nozzle or liquid that has been discharged from the collective nozzle head are respectively storable, along the transporting route.

A fourteenth aspect of the invention is a biological material fixed region treatment apparatus wherein a light reception device, which receives light from the transport storage section, is provided at a predetermined position along the transporting route of the queued route transporting device.

A fifteenth aspect of the invention is a biological material fixed region treatment method comprising: a fixing step for fixing a predetermined biological material to a fixing region such that it is associated with a predetermined position by a predetermined relationship; an enclosing step for forming a biological material fixed region enclosing tip by enclosing within a tip form vessel which has an installation opening part that is installable to one or a plurality of consecutive nozzles that perform suction and discharge of gas, and an opening, through which inflow and outflow of fluid is possible by means of the suction and discharge of gas, the fixing region fixed with the biological material such that the fixing region is able to make contact in an immovable state with the fluid that has flown into the tip form vessel from the opening; and a reaction step for moving a nozzle to which one or two or more of the biological material fixed region enclosing tips has been installed to a-predetermined liquid storage section, and bringing into contact and reacting the biological material fixed to the fixing region and a solution stored in the liquid storage section by controlling the operation of suction and discharge, which comprises the amount of suction and discharge via the nozzle, the speed, the frequency, the time, and the location, based on the structure of the biological material fixed region enclosing tip, the material conditions comprising the type of biological material that is fixed to the fixing region or is present in the solution, the concentration, the amount of solution, or the position coordinate which includes the storage position of the solution, and the processing contents.

A sixteenth aspect of the invention is a biological material fixed region treatment method that, following the reaction step, has a light reception step for receiving light from the fixing region of the biological material fixed region enclosing tip.

A seventeenth aspect of the invention is a biological material fixed region treatment method wherein the reaction step has a temperature raising and lowering step for raising and lowering the temperature within the biological material fixed region enclosing tip.

An eighteenth aspect of the invention is a biological material fixed region treatment method wherein the fixing step is performed by distributing in a fixing region provided on an internal surface of the tip form vessel, the biological material that has passed through a distribution opening provided in the tip form vessel, and the enclosing step is performed by covering the distribution opening with a lid member, which is attached from outside of the tip form vessel.

Effects of the Invention

According to the first aspect of the invention, the fixing region which is fixed or is fixable with various types of biological materials, enables processing to be performed while the fixing region is enclosed in an immovable state with respect to the tip form vessel. Consequently since the fixing region is immovable with respect to the tip form vessel, the various positions on the fixing region can be specified accurately and reliably. Definitely/positively/accurately.

Furthermore, according to the present aspect of the invention, in regard to the fixing region in which a variety of types of biological materials are fixed or are fixable, the enclosing and the removal thereof is performed by a separate route to the route in which suction and discharge of fluid, or the material that is suspended in the fluid, is performed. Consequently, a process for separating the fluid and the fixing region, for example the carrier attachment control and the like, is made unnecessary, the complex reaction process is simplified, and processing can be easily executed by a small-scale device configuration.

According to the present aspect of the invention, by merely performing suction and discharge of fluid while enclosing the fixing region within the tip form vessel, and by moving the tip form vessel, a variety of processes, for example, reaction, washing, temperature control, separation, stirring, dispensing, clarifying, isolation, elution, and extraction can be performed, and therefore, processing can be performed efficiently, quickly, and easily.

Furthermore, according to the present aspect of the invention, since the reaction with the biological material fixed to the fixing region up until measurement can be performed while enclosed within the tip form vessel, the target process can be performed consistently, without being manually handled, and automatically, and therefore, a process that has a high reliability can be performed with certainty. Moreover, according to the present aspect of the invention, by finely setting the aspect of the suction and discharge, for example the speed, the volume, and the time, based on the process contents and the shape of the tip and the like, then reliability can be increased, and it can be made to handle a variety of processes. Therefore it has generality and diversity.

According to the second aspect of the invention, in addition to the effects described for the first aspect, the fixing region is provided on the face form carrier that is detachably attached inside the tip form vessel and is formed in a size where it can be inserted from the carrier insertion opening. Therefore, regarding the fixing process for the biological material, after performing this outside the tip form vessel, it can be enclosed and hence processing is simplified. Furthermore, by using the carrier insertion opening in common with the installation opening part, forming of the tip form vessel is simplified. Moreover, time and effort for manufacture can be reduced. Furthermore, since the area of the opening portion is small, liquid spill and the like can be reliably prevented making handling easy.

By providing the carrier insertion opening part separate to the installation opening part, a large carrier which is not restricted by the size of the nozzle can be inserted. Hence various types of processing are possible giving wide used.

Furthermore, since the plate-shaped carrier is attached so as to enable contact with the liquid, this can be made to reliably contact with the liquid that has been introduced to inside the tip form vessel.

Moreover, since the carrier is attached so that it is immovable with respect to the tip form vessel, there is no influence on the position of the carrier due to the introduction of liquid, and hence in processes accompanying the suction and discharge of liquid, reliable measurements can be performed.

According to the third aspect of the invention, in addition to the abovementioned effects, the distribution opening part capable of passing the biological material and distributing with respect to the fixing region, is provided on the tip form vessel, and the biological material is distributed through the distribution opening part.

Consequently, it is not necessary to take out the fixing region to outside of the tip form vessel in order to perform the fixing process of the biological material, and there is no direct contact with a persons hand. Hence processing with a high reliability can be performed.

Moreover, since it is not necessary to determine the nozzle installation opening part in consideration of the size of the carrier, there is no need to use special order items for the nozzle, and hence manufacturing cost can be kept down.

According to the fourth aspect of the invention and the eighteenth aspect of the invention, by providing the fixing region on the internal surface of the tip form vessel, it is not necessary to use a separately manufactured carrier. Hence the number of parts can be reduced, and manufacturing costs can be reduced. Furthermore, since the internal wall is made the fixing region, the flow of fluid is not disturbed, and smooth suction and discharge can be performed.

According to the fifth aspect of the invention, within the tip form vessel, the volume of the space which is possible between the surface of the fixing region enclosed in the tip form vessel and the internal surface of the tip form vessel, is kept to the volume of the liquid used for processing (a minimum amount). As a result contact between the liquid drawn in to inside the tip form vessel, and the whole surface of the carrier is possible, so that with respect to a minimum amount of liquid, handling of a high reliability is possible.

According to the sixth aspect of the invention, since the fixing region is made so that it is formed on one surface of the plate-shaped carrier or the thin film form carrier provided separate to the tip form vessel, the biological material can be easily fixed. Furthermore, by covering the opening formed in the tip form vessel by means of the carrier, the fixing region can be reliably enclosed inside the tip form vessel.

According to the seventh aspect of the invention, an electroconductive member having a predetermined electrical resistance value is formed on the entire, or on a part of, the wall of the tip form vessel. By flowing an electrical current to the electroconductive member that is formed on the entire, or on a part of, the wall of the tip form vessel, and performing heat generation of the electroconductive member, and hence heating or cooling the fixing region and the liquid stored in the tip form vessel, temperature control of the reaction can be performed.

Consequently, compared to a case where a heating device, such as a heater, is provided on the outside of the wall of the tip form vessel, since it is directly making contact with the inside of the tip form vessel, the reflection of heat by the wall is prevented, the heat can be more efficiently transmitted with respect to the inside of the tip form vessel, the thermal efficiency is high, and an accurate temperature control can be performed.

Furthermore, since the wall of the tip form vessel is formed by an electroconductive member, the thermal efficiency is high, it is not necessary to provide a heating device that is larger than necessary, such as a metallic block, to the outside of the tip form vessel, and it is sufficient to only provide the driving device to the exterior. Consequently, the structure of the exterior is simplified, and the entire device scale can be reduce.

Since an optical temperature raising and lowering body can be provided to the tip form vessels beforehand, it is not necessary to provide a heating device that satisfies a variety of conditions, to the exterior, and it has generality and diversity.

Since the electroconductive member directly makes contact with the inside of the tip form vessel, temperature control of the liquid can be performed with a high accuracy and faithfulness.

The time from applying the signal to the tip form vessel and the electroconductive member for heating or cooling with respect to the liquid until the liquid temperature becomes a uniform temperature distribution is shortened, and the process can be quickly and efficiently performed.

Furthermore, since in particular the temperature and the time of hybridization can be controlled in parallel or in series to the suction and discharge or the movement processing, then processing up until cleaning of the array, detection, and measurement can be controlled consistently.

According to the eighth aspect of the invention, the biological material fixed region enclosing tip, in which a fixing region, to which a biological material is fixed or is fixable, is enclosed within the tip form vessel, is installed to the nozzle, and the amount, the speed, the frequency, or the position of the suction and discharge with respect to the nozzle is controlled based on the material conditions, which comprise the shape of the tip thereof, the shape of the fixing region, the type of the biological material that is fixed on the fixing region or is to be suspended, the amount of liquid, and the coordinate position which includes the storage position of the liquid, and the processing conditions, which comprise the time and the temperature of incubation, or the processing contents.

Consequently, according to the present aspect of the invention, as well as using a biological material fixed region enclosing tip with a predetermined structure, by performing fine controls with respect to the suction and discharge, processes such as reaction, stirring and cleaning, on the biological material which is fixed or is fixable to the fixing region that is enclosed within the tip, can be easily, consistently, quickly, and efficiently performed with a high reliability. Furthermore, according to the present aspect of the invention, by changing the contents of the control, a variety of processes can be handled, and therefore, it has generality and diversity.

According to the ninth aspect of the invention or the sixteenth aspect of the invention, by receiving light from the fixing region, processing up until measurement can be performed more consistently, quickly, and efficiently with a high reliability.

According to the tenth aspect of the invention, within the tip form vessel, by suppressing the capacity of the space capable of storing the liquid in a state where the fixing region is enclosed in the tip form vessel, the contact between the liquid suctioned into the tip form vessel and the entire surface of the fixing region is made possible, and handling with a high reliability with respect to the microamount of liquid is made possible.

According to the eleventh aspect of the invention or the seventeenth aspect of the invention, temperature control is performed on the biological material fixed region enclosing tip, and consequently on the fixing region enclosed therein, by approaching a temperature raising and lowering body from the exterior. Consequently, compared to a case where temperature control is performed and reaction with the fixing region is performed by heating a vessel provided outside the tip, the reaction can be more efficiently performed with certainty. Moreover, since temperature control can be performed on the biological material fixed region enclosing tip, as it is, this can be performed with a simple control, and is thus suitable for automation.

According to the twelfth aspect of the invention, the collective nozzle head and the individual nozzle head is simultaneously movable in the row direction, and a queued route transporting device having a transport route provided with the row transporting route and the column transporting route, is provided on the movement route of the collective nozzle head and the individual nozzle head. Consequently, as a result of the transporting device, it is processable by either the collective nozzle head or the individual nozzle head, a plurality of nozzles and a suction and discharge mechanism are not arranged in a queue form, and a variety of complex processes are made possible by a simple and compact structure using a small number of nozzles.

Furthermore, at the time the suction and discharge process is performed with respect to a plurality of processing subjects, in regard to the common processing items, by collectively performing processing using the collective nozzle head, and in regard to the processing items in which it is necessary to individually perform processing, by performing processing individually using the individual nozzle head, a variety of processes can be efficiently and quickly performed.

In particular, in regard to a case where a measurement is performed individually, it is suitable for a case where a necessary reagent is added directly before the measurement thereof, or a case where a reagent with a need for maintaining a predetermined temperature is added directly before processing that is performed individually.

According to the thirteenth aspect of the invention, as well as demonstrating the same effects as the aforementioned twelfth aspect of the invention, since suction and discharge of the collective nozzle and the individual nozzle can be simultaneously performed with the same suction and discharge mechanism, the structure is simpler.

According to the fourteenth aspect of the invention, by providing a light reception device at, at the very least, one position on the transporting route of the queued route transporting device, processes that handle the nozzles that are processed with a plurality of consecutive nozzles, and serial measurement using a small number of light reception devices, can be performed. Consequently, the device can be simplified. In particular, since reagents that only become necessary directly before light reception by the light reception device, can be serially charged by the individual nozzle head directly before light reception, light reception can be performed efficiently with a high reliability.

According to the fifteenth aspect of the invention, the biological material fixed region enclosing tip, in which a fixing region, to which a biological material is fixed or is fixable, is enclosed within the tip form vessel, is installed to the nozzle, and the amount, the speed, the frequency, or the position of the suction and discharge with respect to the nozzle is controlled based on the material conditions, which comprise the structure of the tip thereof, the type of the biological material that is fixed on the fixing region or is to be suspended, the amount of liquid, and the coordinate position which includes the storage position of the liquid, and the processing conditions, which comprise the time and the temperature of incubation, or the processing contents. Consequently, according to the present aspect of the invention, as well as using a biological material fixed region enclosing tip with a predetermined structure, by performing fine controls with respect to the suction and discharge, processes such as reaction with the suctioned liquid, the stirring thereof, and cleaning, on the biological material which is fixed or is fixable to the fixing region that is enclosed within the tip, can be easily, consistently, quickly, and efficiently performed with a high reliability. Furthermore, by changing the contents of the control, a variety of processes can be handled, and therefore, it has generality and diversity.

BEST MODE FOR CARRYING OUT THE INVENTION

According to the present invention, as well providing an enclosing section to the tip form vessel, and enclosing a biological material fixed region in which the biological material is fixed or is fixable to a predetermined position, such that it becomes able to make contact with the fluid, by making the fixed positions measurable from the exterior, a consistent automation of a process from a reaction between the biological material and the biological material contained in the liquid that has flowed in until arriving at the measurement, is achieved.

Next, the embodiments of the present invention are explained based on the drawings. The explanation of the embodiments should in no way be interpreted as limiting the present invention unless particularly specified.

Figure 1:
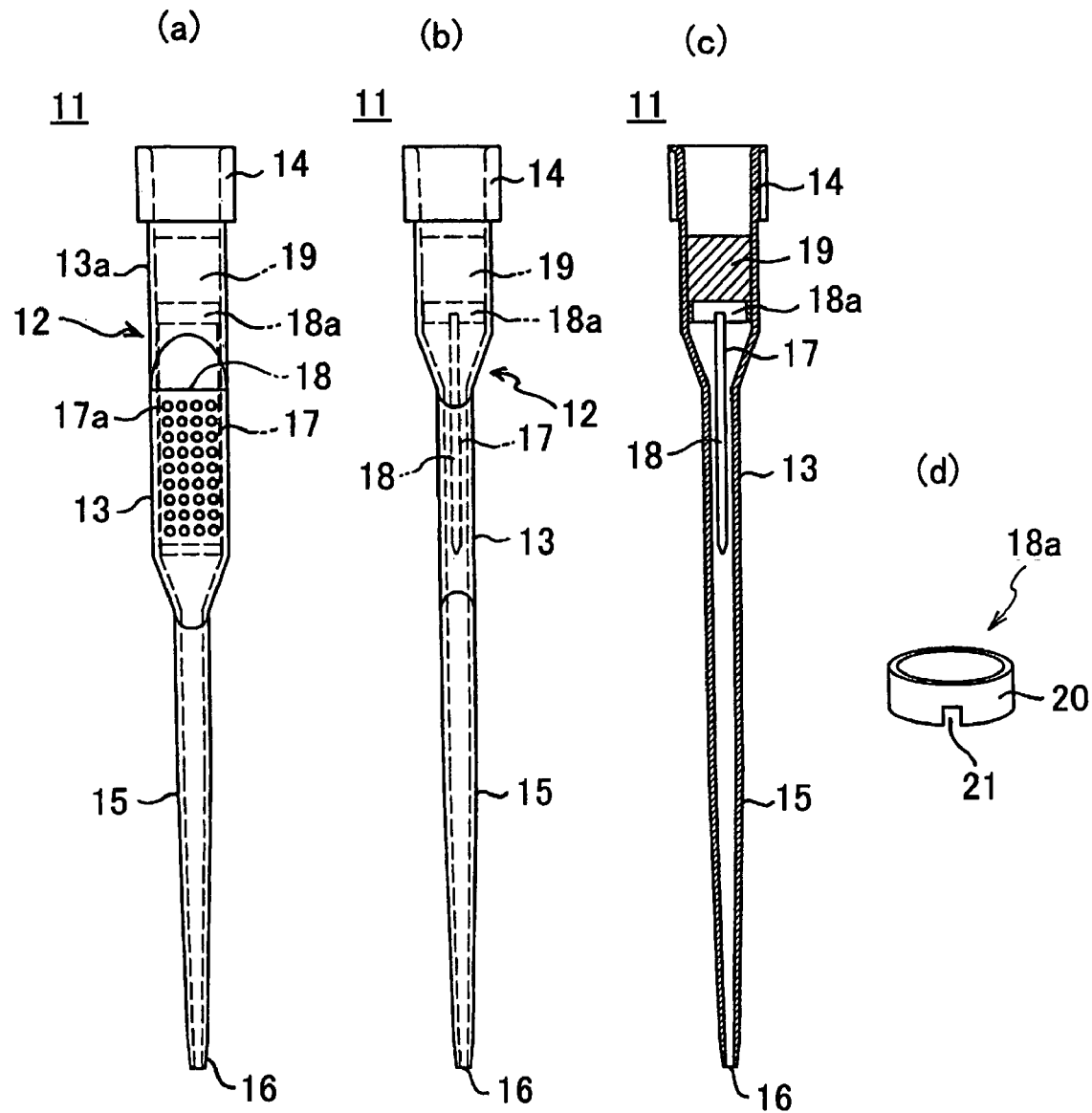
FIG. 1 is a drawing showing a biological material fixed region enclosing tip according to a first embodiment.

FIG. 1(*a*) to FIG. 1(*d*) show a biological material fixed region enclosing tip 11 according to a first embodiment of the present invention. FIG. 1(*a*) shows a front view of the biological material fixed region enclosing tip 11, which is one having a tip form vessel 12 which is translucent, that has a thin approximate prism shape fixing region forming section 13, and a narrow tube 15 that is formed narrower than the fixing region forming section 13 and a nozzle to which it is installed (not shown in the figure). An upper end 13*a* of the fixing region forming section 13 is formed in a cylinder shape, and on the upper edge thereof is provided a cylinder shape installation opening part 14 that is to be installed to a nozzle which is not shown in the drawing, that performs suction and discharge of gas. An opening 16, through which fluid inflow and outflow is possible by means of the suction and discharge of gas, is provided on the end of the narrow tube 15. The fixing region forming section 13 has a size such that a plate-shaped carrier 18 provided with a fixing region 17 can be passed through the installation opening part 14 of the upper end 13*a* and inserted. The installation opening part 14 also corresponds to the carrier insertion opening. On the plate-shaped carrier 18, various types of biological materials determined beforehand are fixed or are fixable to previously determined positions 17*a*.

An annular attachment member 18*a* serving as the enclosing section, is engaged with the inside of the upper end 13*a* and thus attached to the tip form vessel 12. The plate-shaped carrier 18 is immovably attached with respect to the annular attachment member 18*a* and hence with respect to tip form vessel 12, as is evident from the side view of FIG. 1(*b*) and the cross-section of FIG. 1(*c*).

A filter 19 capable of passing a gas, is installed on the somewhat lower side of the installation opening part 14 on the inside of the upper end 13*a* of the fixing region forming section 13, and on the upper side of the annular attachment member 18*a*.

As shown by the perspective drawing of FIG. 1(*d*), the annular attachment member 18*a* is provided with an annular rim 20, and opposed square shape cut outs 21 on the bottom side of the annular rim 20 on either side of the central axis. The annular attachment member 18*a* is attached so that an upper edge of the plate-shaped carrier 18 is gripped in the portion of the cut outs 21. The aforementioned fixing region is formed on the plate-shaped carrier 18.

Figure 2:
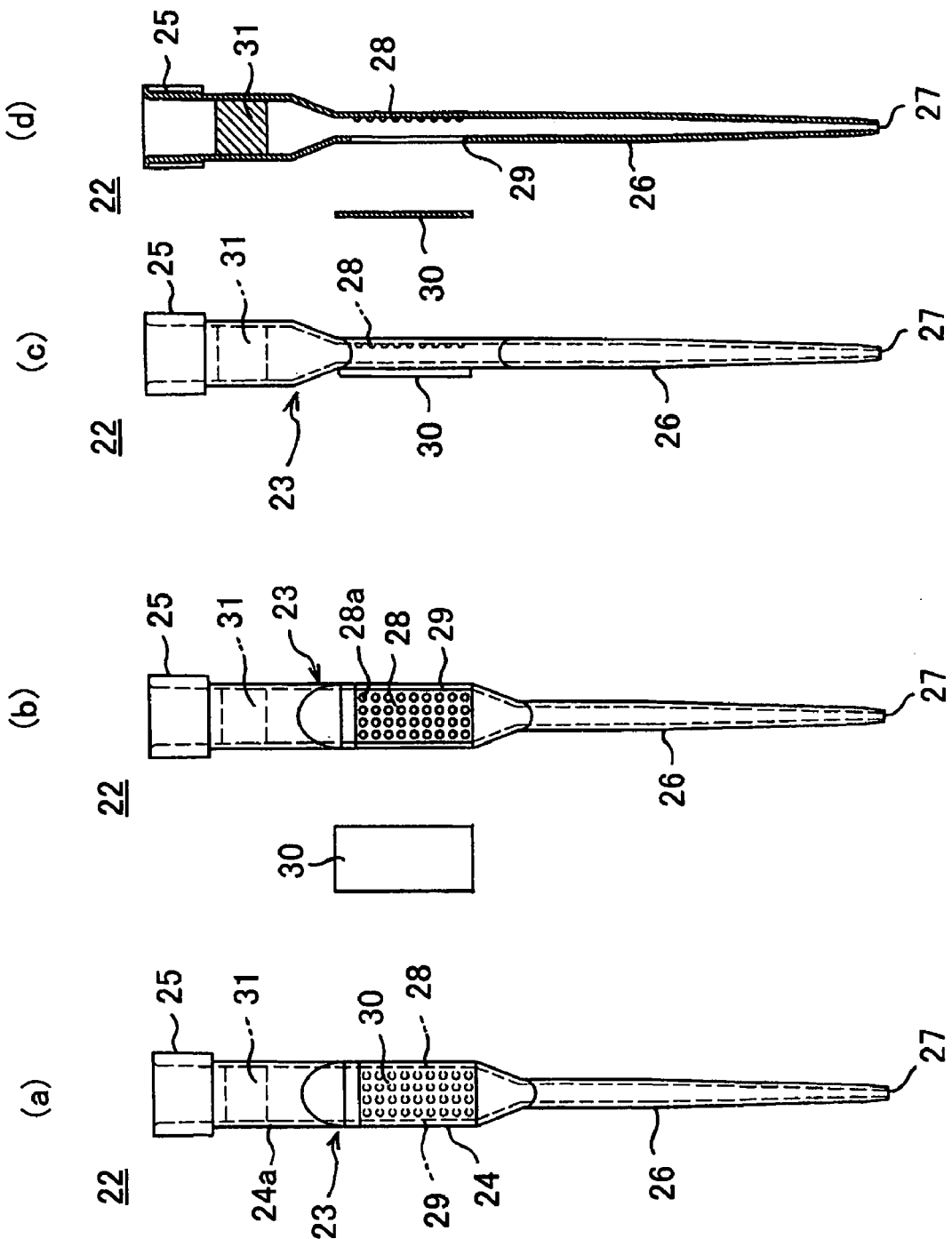
FIG. 2 is a cross-sectional view showing a biological material fixed region enclosing tip according to a second embodiment.

To continue, FIG. 2(*a*) to FIG. 2(*d*), show a biological material fixed region enclosing tip 22 according to a second embodiment of the present invention. FIG. 2(*a*) shows a front view of the biological material fixed region enclosing tip 22. The biological material fixed region enclosing tip 22 has a tip form vessel 23 which is translucent, and has a thin approximate prism shape fixing region forming section 24, and a narrow tube 26 that is formed narrower than the fixing region forming section 24 and a nozzle to which it is installed (not shown in the figure). An upper end 24*a* of the fixing region forming section 24 is formed in a cylinder shape, and on the upper edge thereof is provided a cylinder shape installation opening part 25 that is to be installed to a nozzle which is not shown in the drawing, that performs suction and discharge of gas. An opening 27, through which fluid inflow and outflow is possible by means of the suction and discharge of gas, is provided on the end of the narrow tube 26.

On the largest side face of the side faces of the fixing region forming section 24, which has the greatest area, is formed a fixing region 28 to which a predetermined biological material is fixed or is fixable at a previously determined position. Furthermore, the largest side face facing the aforementioned largest side face of the fixing region forming section 24 has a distribution opening section 29 capable of distributing the predetermined biological material with respect to the fixing region 28. Moreover, regarding the distribution opening section 29, in order to enclose the fixing region 28 inside the tip form vessel 23, this is made to be closable by a plate-shaped lid member 30 serving as an enclosing section. Furthermore, on the upper portion 24*a* of the fixing region forming section 24 is provided a filter 31 through which gas can pass. FIG. 2(*b*) and FIG. 2(*d*) show a state where the lid member 30 is removed from the tip form vessel 23. Regarding the size of the distribution opening section 29, this must have a shape or size such that a predetermined biological material can be distributed by a dispensing tip or the like, in the fixing region 28. For example, the distribution opening section 29 is formed so that this becomes equal to the area and the shape of the fixing region 28. In the figure reference symbol 28*a* indicates a fixing position or a fixable position for the predetermined biological material.

Figure 3:
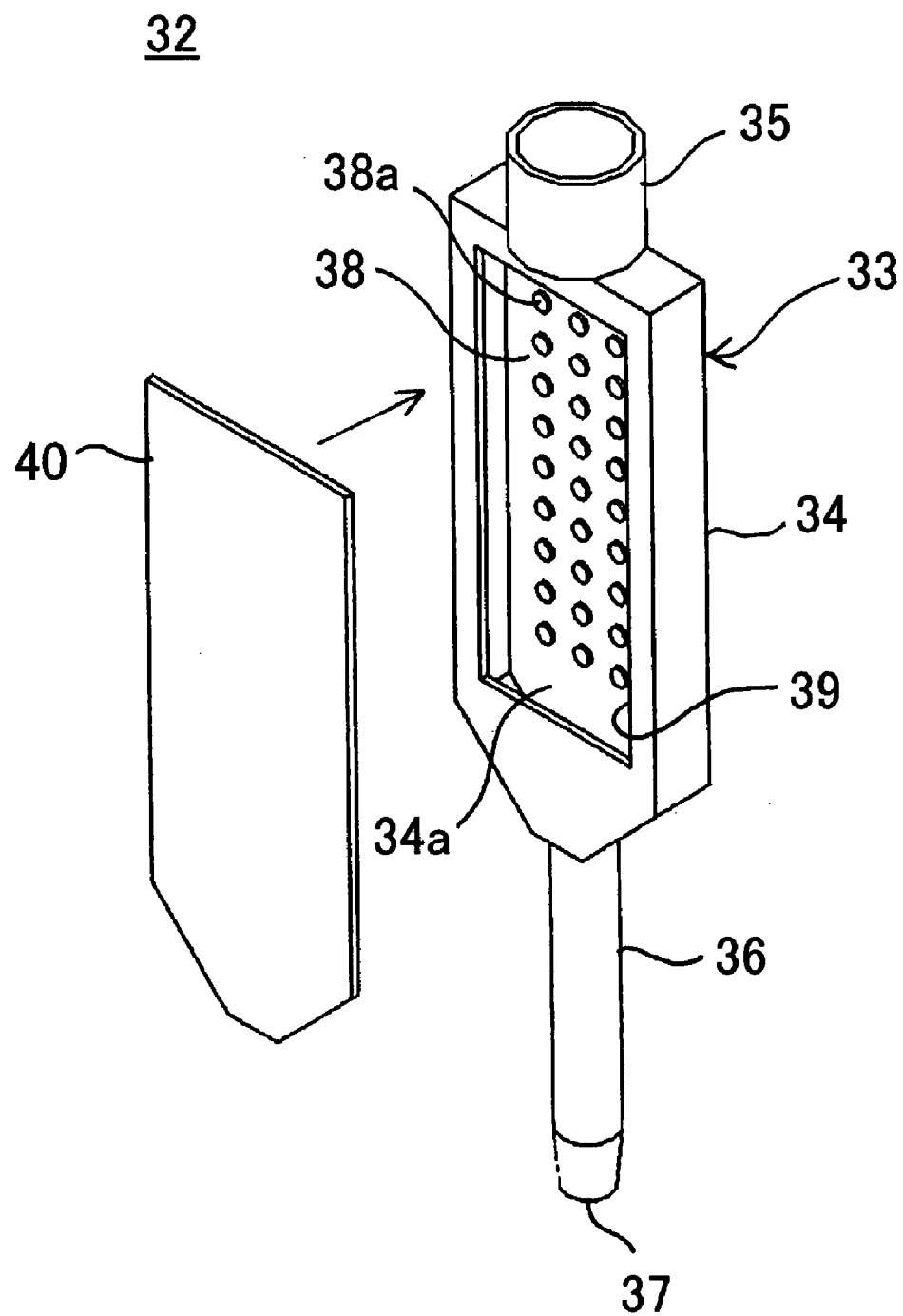
FIG. 3 is an exploded perspective view showing a biological material fixed region enclosing tip according to another aspect of the second embodiment.

FIG. 3 shows an exploded perspective view of a biological material fixed region enclosing tip 32 according to another aspect of the second embodiment of the present invention. The biological material fixed region enclosing tip 32 has a tip form vessel 33 which is translucent, and has a thin approximate prism shape fixing region forming section 34, and a narrow tube 36 that is formed narrower than the fixing region forming section 34 and a nozzle to which it is installed (not shown in the figure). An upper side of the fixing region forming section 34 has a cylinder shape installation opening part 35 that is to be installed to the nozzle which is not shown in the drawing, that performs suction and discharge of gas. An opening 37, through which fluid inflow and outflow is possible by means of the suction and discharge of gas, is provided on the end of the narrow tube 36. On the largest side face 34*a* of the side faces of the fixing region forming section 34, which has the greatest area, is formed a fixing region 38 to which a predetermined biological material is fixed or is fixable at a previously determined position.

Furthermore, the largest side face facing the aforementioned largest side face 34*a* of the fixing region forming section 34 has a distribution opening section 39 capable of distributing the predetermined biological material with respect to the fixing region 38. Moreover, regarding the distribution opening section 39, in order to enclose the fixing region 38 inside the tip form vessel 33, this is made to be closable by a plate-shaped lid member 40 serving as an enclosing section, that is attached to the outer wall of the tip form vessel 33. Regarding the size of the distribution opening section 39, this must have a shape or size such that a predetermined biological material can be distributed by a dispensing tip or the like, in the fixing region 38. For example, the distribution opening section 39 is formed so that this becomes equal to the area and the shape of the fixing region 38. In the figure reference symbol 38a indicates a fixing position or a fixable position for the predetermined biological material.

Figure 4:
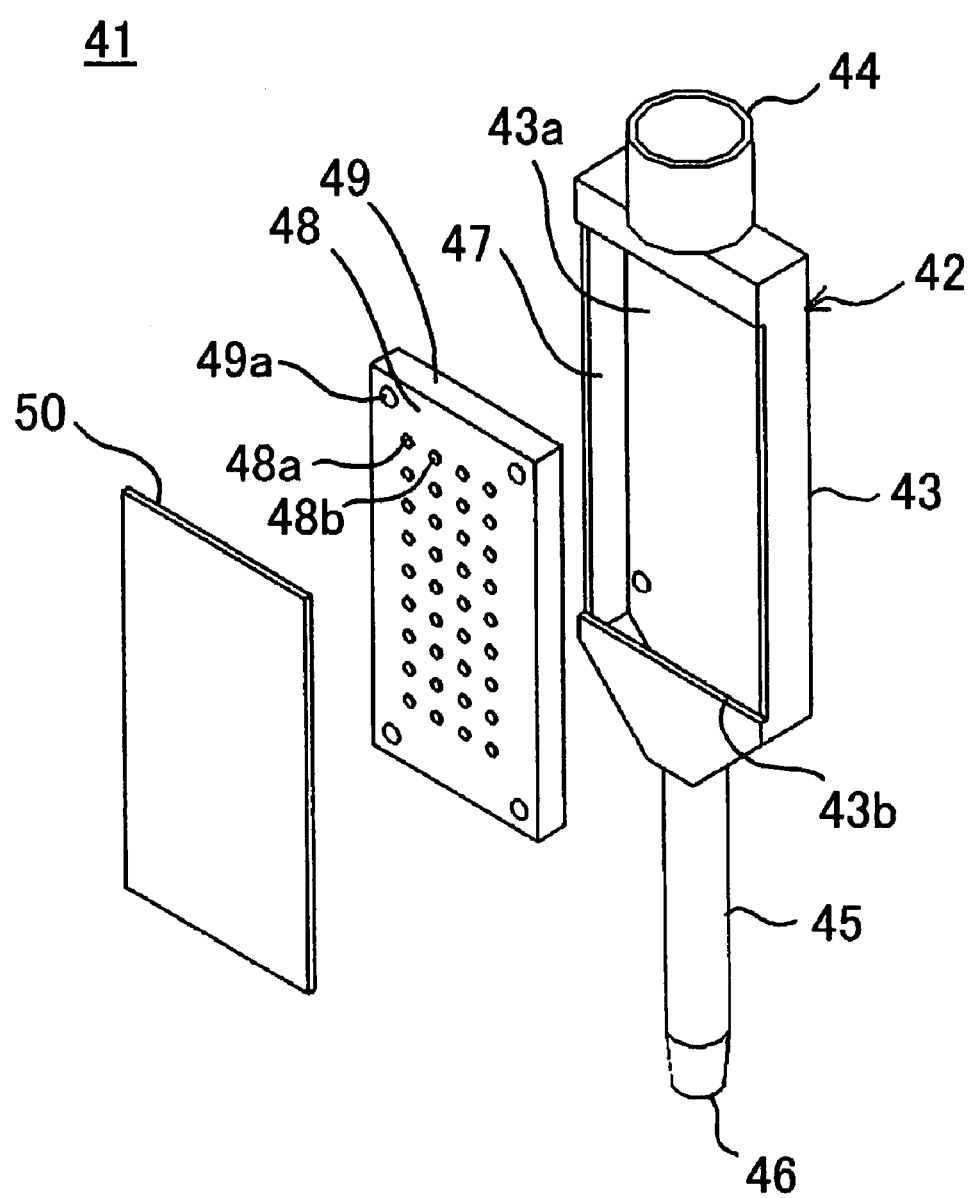
FIG. 4 is an exploded perspective view showing a biological material fixed region enclosing tip according to a fourth embodiment.

FIG. 4 is an exploded perspective view and perspective view showing a biological material fixed region enclosing tip 41 according to a third embodiment.

The biological material fixed region enclosing tip 41 has a tip form vessel 42 which is translucent, and has a thin approximate prism shape fixing region forming section 43, and a narrow tube 45 that is formed narrower than the fixing region forming section 43 and a nozzle to which it is installed (not shown in the figure). An upper side of the fixing region forming section 43 has a cylinder shape installation opening part 44 that is to be installed to the nozzle which is not shown in the drawing, that performs suction and discharge of gas. An opening 46, through which fluid inflow and outflow is possible by means of the suction and discharge of gas, is provided on the end of the narrow tube 45. The fixing region forming section 43 has a size capable of storing the plate-shaped carrier 49 with the fixing regions 48 provided on one flat face thereof. The plate-shaped carrier 49 is attached to the inner wall of largest side face 43a of the side faces of the fixing region forming section 43, which has the greatest area, so as to be immovable by means of attaching members 49a such as screws which are provided in four corners of the plate-shaped carrier 49. Furthermore, on the side face facing the largest side face 43a there is provided a carrier insertion opening 47 for storing the plate-shaped carrier 49 from the outside.

The plate-shaped carrier 49 is for example formed by a slide glass. The size of the slide glass is for example 6.2 mm×30 mm, and the surface is processed in order to fix various oligonucleotides serving as DNA probes. At this time, when enclosed in the fixing region forming section 43, the space formed in the fixing region forming section 43 forms a space with around 0.5 mm or less between the walls, and having a volume approximately coinciding with the minimum volume for handling, so that experiments with good efficiency are possible.

Furthermore, to cover the carrier insertion opening 47, a thin plate lid member 50 for enclosing the plate-shaped carrier 49 is provided. The lid member 50 corresponds to the enclosing member. On a portion corresponding to the largest side face of the fixing region forming section 43 of the approximate rectangular shape there is provided an engaging portion 43b which engages the lid member 50.

Figure 5:
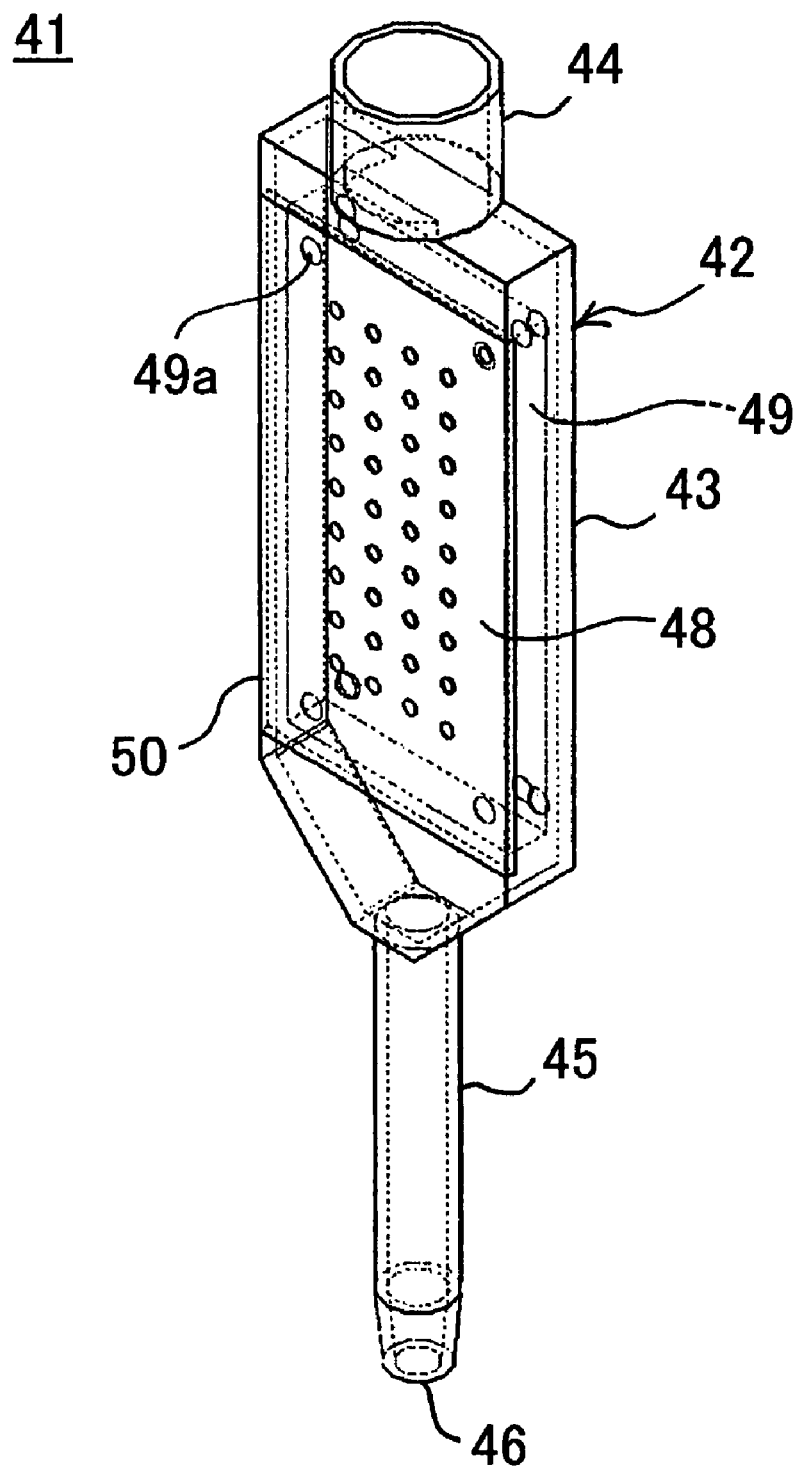
FIG. 5 is a perspective view of a biological material fixed region enclosing tip according to the fourth embodiment.

The biological material fixed region enclosing tip 41 in a state with the plate-shaped carrier 49 having the fixing regions 48 stored, and the fixing regions 48 enclosed is shown in FIG. 5.

Figure 6:
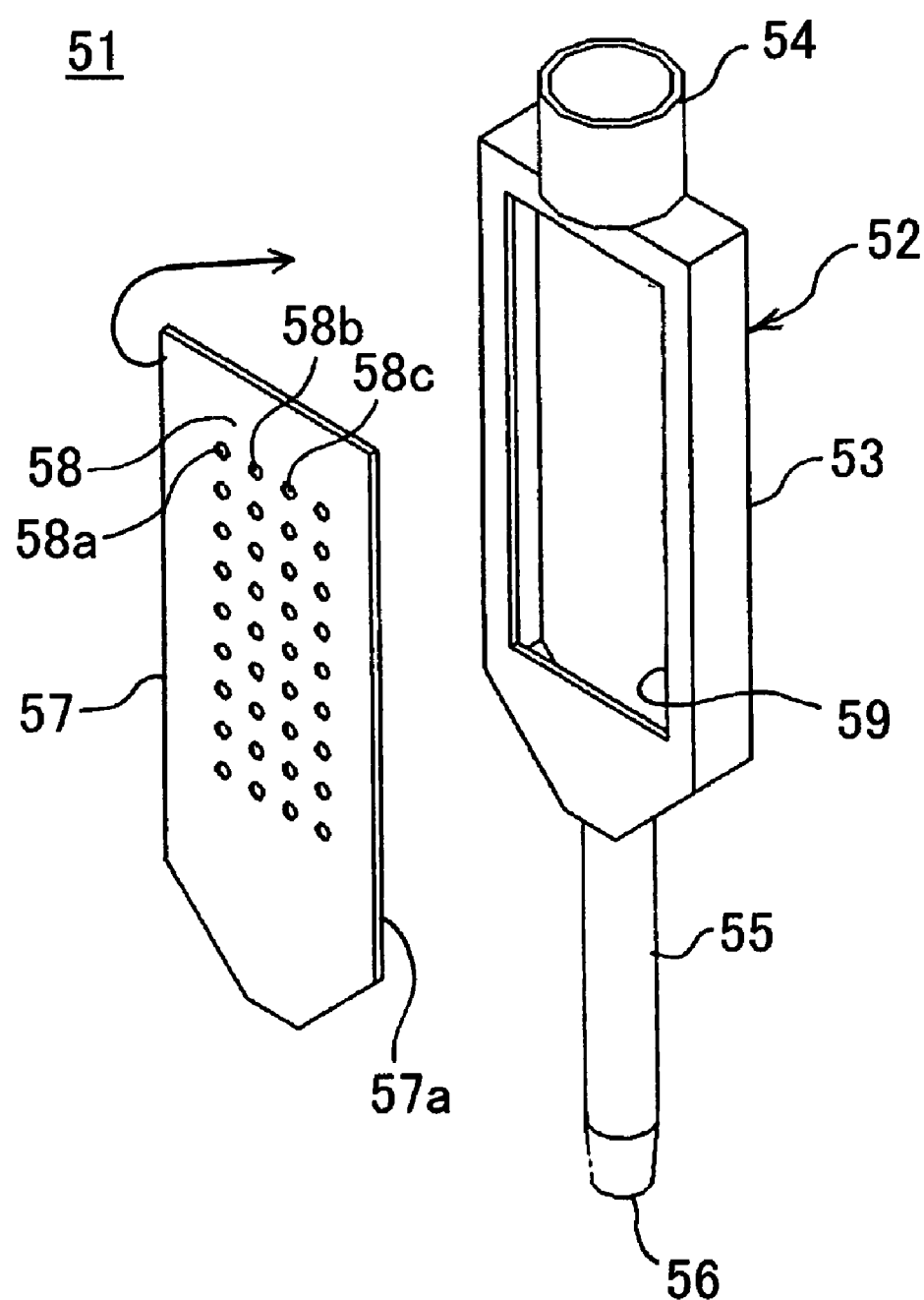
FIG. 6 is an exploded perspective view showing a biological material fixed region enclosing tip according to a fifth embodiment.

FIG. 6 is an exploded perspective view showing a biological material fixed region enclosing tip 51 according to a third embodiment. The biological material fixed region enclosing tip 51 has a tip form vessel 52 which is translucent, and has a thin approximate prism shape fixing region forming section 53, and a narrow tube 55 that is formed narrower than the fixing region forming section 53 and a nozzle to which it is installed (not shown in the figure). An upper side of the fixing region forming section 53 has a cylinder shape installation opening part 54 that is to be installed to the nozzle which is not shown in the drawing, that performs suction and discharge of gas. An opening 56, through which fluid inflow and outflow is possible by means of the suction and discharge of gas, is provided on the end of the narrow tube 55.

A fixing region 58 to which a predetermined biological material is fixed or is fixable at a previously determined position, is formed on one plane face of a plate-shaped carrier 57 serving as a plane form carrier. The rear face of the plane face is to be covered with an electrically conductive thin film 57a, and by flowing an electrical current to the electrically conductive thin film 57a, this can be heated. Furthermore, of the side faces of the tip form vessel 52, on the largest side face having the largest area, there is provided a fluid contact opening part 59 for enabling contact between the fixing region 58 of the plane form carrier 57 and the fluid that has been introduced from the opening 56. So that the fixing region 58 of the plane form carrier 57 forms an inner wall of the tip form vessel 52, the plane form carrier 57 is attached by an adhesive or screws or the like to the outer wall of the tip form vessel 52 so as to close off the fluid contact opening part 59. Consequently, the plane form carrier 57 corresponds to the enclosing section.

Figure 7:
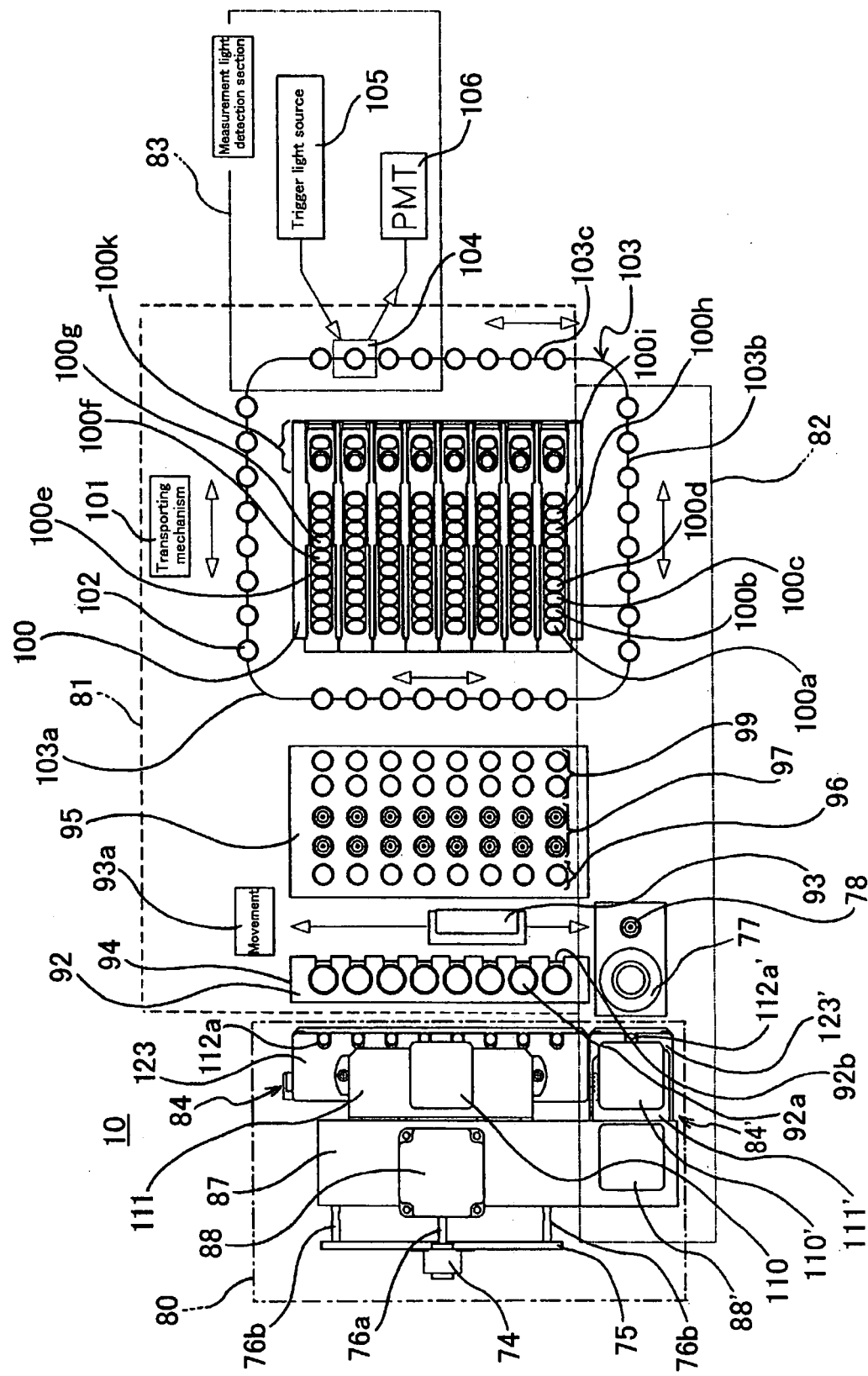
FIG. 7 is a plan view showing an entire biological material fixed region treatment apparatus according to a sixth embodiment.

FIG. 7 is a planar schematic view representing an entire biological material fixed region treatment apparatus 10 according to a fourth embodiment of the present invention.

The biological material fixed carrier treatment apparatus 10 has: a biological material fixed region enclosing tip processing device 80, which has a suction and discharge mechanism, and installs the biological material fixed region enclosing tip 35 on a nozzle, and performs a suction and discharge process with respect to the biological material fixed region enclosing tip 32; a tip processing region 81 for performing, suction and discharge with respect to the biological material fixing region, dispensing into an exterior vessel, stirring, washing, extraction, transport, reaction, or the like, by performing suction or discharge of a suspension containing various specimens, reagents, or the like, within the biological material fixed region enclosing tip 35; a reagent dispensing region 82 for dispensing a reagent for measurement, to within the biological material fixed region enclosing tip by using a single nozzle possessed by the biological material fixed region enclosing tip processing device 80; and a measurement region 83 that obtains optical information for executing measurement in regard to the biological material fixed region that is enclosed within the biological material fixed region enclosing tip 32.

In regard to the biological material fixed region enclosing tip processing device 80 shown in FIG. 7 and FIG. 8, suction and discharge of gas is performed using a nozzle that is communicated with a collective suction and discharge mechanism and an individual suction and discharge mechanism. The biological material fixed region enclosing tip processing device 80 has a collective nozzle head 84 that has a plurality (eight consecutive in this example) of nozzles 117 that are arranged in the column direction (the vertical direction in the drawing), and an individual nozzle head 84' that has a single nozzle that performs suction and discharge independently to the collective nozzle head 84. In regard to the collective nozzle head 84, as opposed to the suction and discharge being simultaneously performed by the collective suction and discharge mechanism with respect to the plurality of consecutive nozzles 117, the suction and discharge is performed with respect to the nozzle (one in this example) of the individual nozzle head 84' independently to the eight consecutive nozzles 117 by an individual suction and discharge mechanism. In the drawing, the reference symbols of the components, or the like, that belong to the individual nozzle head 84' are indicated by attaching a dash to the reference symbol of the components, or the like, that belong to the corresponding collective nozzle head 84.

Figure 8:
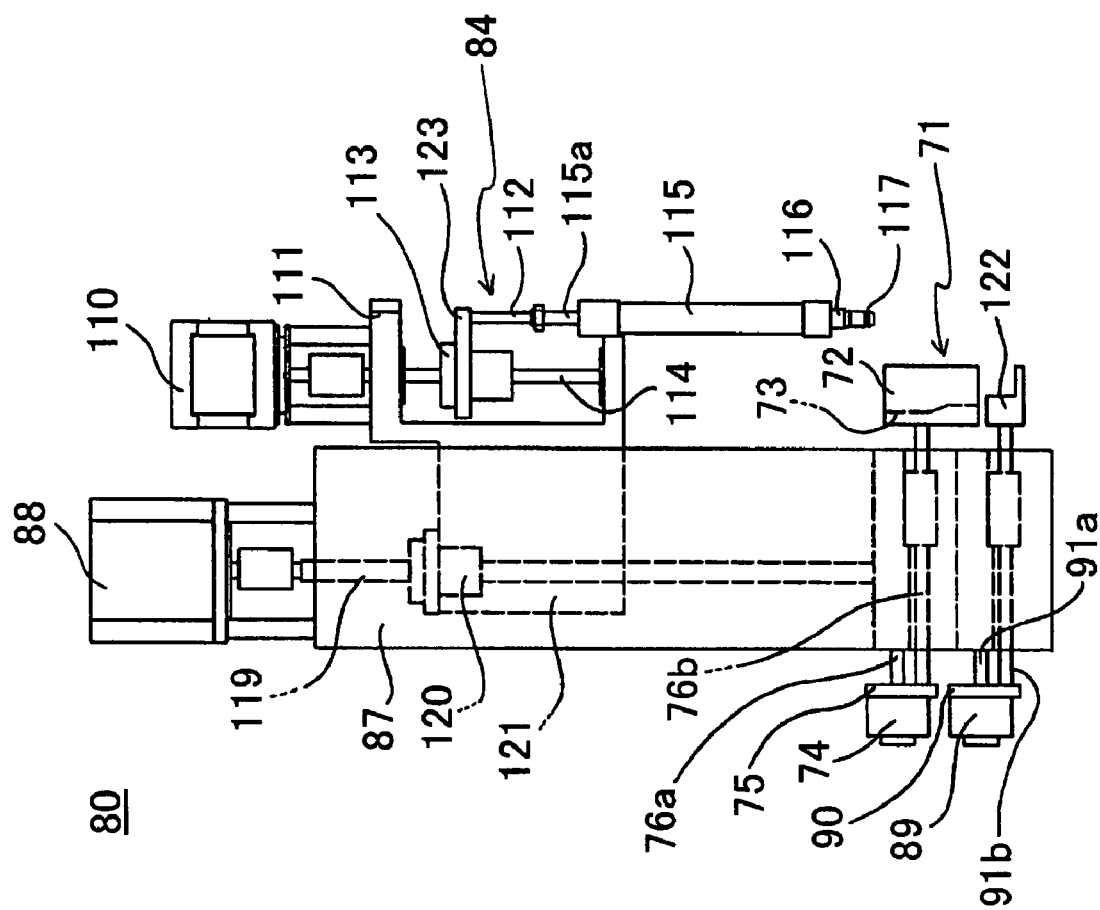
FIG. 8 is a side view showing a biological material fixed region enclosing tip treatment apparatus according to a sixth embodiment.

In FIG. 8, only the collective suction and discharge mechanism of the collective nozzle head 84 is shown. This collective suction and discharge mechanism has an engaging section 116 that is provided to a somewhat upper section than the lower end of the nozzle 117, and a rod 112 for sliding a plunger 115*a* within a cylinder 115 that is joined to the nozzle 117. Furthermore, the eight rods 112 are installed in eight respective notch sections that are provided on the edge of a driving plate 123 (reference symbol 123' represents a driving plate of the individual suction and discharge mechanism) in which vertical movement is independently possible for each, such that they sit on eight consecutive end sections 112*a* (reference symbol 112*a*' represents an end portion of the individual suction and discharge mechanism), that have a larger diameter than the diameter of the rods 112 and protrude in the radial direction. Hence, the collective nozzle head 84 and the individual nozzle head 84' simultaneously move in the row direction (the horizontal direction or the left and right directions on the drawing).

Furthermore, as shown in FIG. 8, the driving plate 123 is joined to a nut section 113 that screws to a ball screw 114. The rods 112 are energized in the downward direction at all times by means of a spring that is provided to the cylinder 115. Consequently, the rods 112 are able to be raised by the nut sections 113 in a case where they move in the upward direction, but in a case where they are lowered in the downward direction, they are lowered not as a result of the nut sections 113, but because of the spring force. The ball screws 114 are rotationally driven by a motor 110 (reference symbol 110' represents the motor of the individual suction and discharge mechanism) provided to a cross-sectional U-shaped supporting member 111 (reference symbol 111' represents the supporting member of the individual suction and discharge mechanism), and as a result, the driving plate 123 and the eight rods 112 vertically move.

In regard to the raising and lowering of the nozzle itself, although it is independent of the individual nozzle head 84' and the collective nozzle head 84, the horizontal movement in the row direction (the left and right directions in FIG. 7) is integrated. The individual nozzle head 84' is, in regard to the reagent dispensing region 82, used for dispensing reagents for measurement within the biological material fixed region enclosing tip 32, that are stored within the tip storage section 102. In the reagent dispensing region 82, a reagent storage section 77 that stores predetermined reagents that are suctioned by the nozzle head 84', and a predetermined tip 78, which is in a state where it is installable to the nozzle head 84', for example, a filter-containing tip, are provided. Furthermore, the reagent storage section 77 is, for example, provided with a constant temperature device for retaining the reagents at a constant temperature.

In FIG. 8, the inside of the chassis 87, has a ball screw 119, a nut section 120 that screws to the ball screw 119, and a supporting body 121 that has the supporting member 111, to which the nut section 120 is installed, at one end. Furthermore, on the chassis 87, a motor 88 that rotationally drives the ball screw 119 is provided. By means of a vertical movement mechanism resulting from these components, the nozzle 117 is vertically movable.

A temperature raising and lowering device 71 is provided on the lower side of the chassis 87. In regard to the temperature raising and lowering device 71, it is formed along the column direction such that it has a height and a width that primarily makes it approachable to, or able to make contact with, the fixing region forming section which is principally the eight tips that are installed to the eight consecutive nozzles, it has a heating plate 73 that has a heater in the interior, and nine heating walls 72, which are installed to the heating plate 73, that have a heater in the interior and are provided protruding such that they respectively sandwich the tips from both sides, and this heating plate 72 and these nine heating walls 72 are, as a whole, formed in a comb form. Furthermore, it is preferable for the heating plate 73 to be formed such that it has a shape that is matched to the shape of the tip that becomes the subject of temperature control. Here, the heating plate 73 and the heating walls 72 correspond to the temperature raising and lowering body.

The temperature raising and lowering body 71 approaches, or makes contact with, the tip installed to the nozzle 117 of the collective nozzle head 84, and it has a motor 74 for making it possible to heat the tip, a ball screw 76*a* that is rotationally driven by the motor 74, a nut section 75 that screws onto the ball screw 76*a*, and a movement rod 76*b* that joins the nut section 75 and is movable in the left and right directions in the drawing, and also joins to the heating walls 72 and the heating plate 73.

The bottom side of the temperature raising and lowering device 71 has a motor 89 for making it possible to remove the tip that has been installed to the nozzle 117 of the collective nozzle head 84, a ball screw 91*a* that is rotationally driven by the motor 89, a nut section 90 that screws onto the ball screw 91*a*, and a movement rod 91*b* that joins the nut section 90 and is movable in the left and right directions in the drawing, and which moves a claw 122 in the left and right directions in the drawing.

The biological material fixed region enclosing tip processing device 80 is provided such that it is suspended from the upper side, and it is movably provided by means of an X axis (row direction) movement mechanism not shown in the drawing, which utilizes a direct acting mechanism, such that it covers all regions of the biological material fixed region treatment apparatus 10 and the other necessary regions.

Furthermore, returning to FIG. 7, the tip processing region 81 has: a cartridge vessel 92, which has eight consecutive specimen wells 92*a* that store the suspension in which the specimen is suspended; a matrix form vessel 95, which, as well as storing various tip type columns 96 and 97, has a 5 column×8 row well having a liquid storage section column 99 that stores the product material; and eight cartridge vessels 100 that have a prepackable well 100*a* for storing various reagents or materials that are necessary for executing processing, or storing the resulting material of processing. Amongst the cartridge vessels 101, reference symbol 100*b* represents an incubator well that is provided with a heat block.

Furthermore, barcodes 92*b* are attached to the specimen storage wells 92*a*, that display information relating to the respective specimens thereof. The barcodes 92*b* are read by a barcode reading section 93, which reads the barcode 92*b*, by moving such that it scans. Reference symbol 93*a* is a movement mechanism that drives the barcode reading section 93.

A movable conveyor 103, which is made to surround the surroundings of the eight consecutive cartridge vessels 100, is provided along a square shaped transporting route that has the column transporting routes 103*a* and 103*c* on the movement route of the collective nozzle head 84 of the biological material fixed region enclosing tip processing device 80 along the column direction (the vertical direction or the Y direction in the drawing), which is parallel to the arrangement direction of the eight consecutive nozzles, and a row transporting route 103b on the movement route of the individual nozzle head 84' along the row direction (the horizontal direction or the X direction), which is perpendicular to the arrangement direction.

The conveyor 103 corresponds to the queued route transporting device, and a total of 32 tip storage sections 102, which correspond to the transport storage section, are movably joined together with the conveyor 103, such that they correspond to the spacing between the nozzles. Consequently, in regard to a position such as the one shown in FIG. 7, suction and discharge of liquid with respect to the two columns of tip storage sections 102 arranged on the column transporting routes 103a and 103c are possible by means of the eight consecutive nozzles of the biological material fixed region enclosing tip processing device 80. Furthermore, by means of the series of nozzles of the individual nozzle head 84', which is provided such that suction and discharge is possible independently to the group of eight consecutive nozzles of the collective nozzle head 84 of the biological material fixed region enclosing tip processing device 80, within the transporting route, which has been arranged in a square shape as the queued route transporting device, the row transporting route 103b of the lower side, that is to say, with respect to the selected tip storage sections 102 within the reagent dispensing region 82, reagents that correspond to an object, for example, a substrate liquid, or the like, in chemiluminescence, can be dispensed. In particular, it is dispensed directly before reaction of the PCR reaction liquid, or the like, in PCR preprocessing for a case where DNA extraction is performed. Here, the tip storage sections 102 are parts that store or retain the biological material fixed region enclosing tips with the nozzles 117 detached, so that measurement is possible from outside.

Furthermore, within the measurement region 83, a measurement position 104 is provided within the square shaped transporting route of the queued route transporting device, and in regard to the measurement position 104, excitation light is irradiated within the biological material fixed region enclosing tip by means of the trigger light source 105, and measurement is performed by receiving the generated light at the light receiving section 106. Consequently, processing can be performed according to the processing object for each tip.

Figure 9:
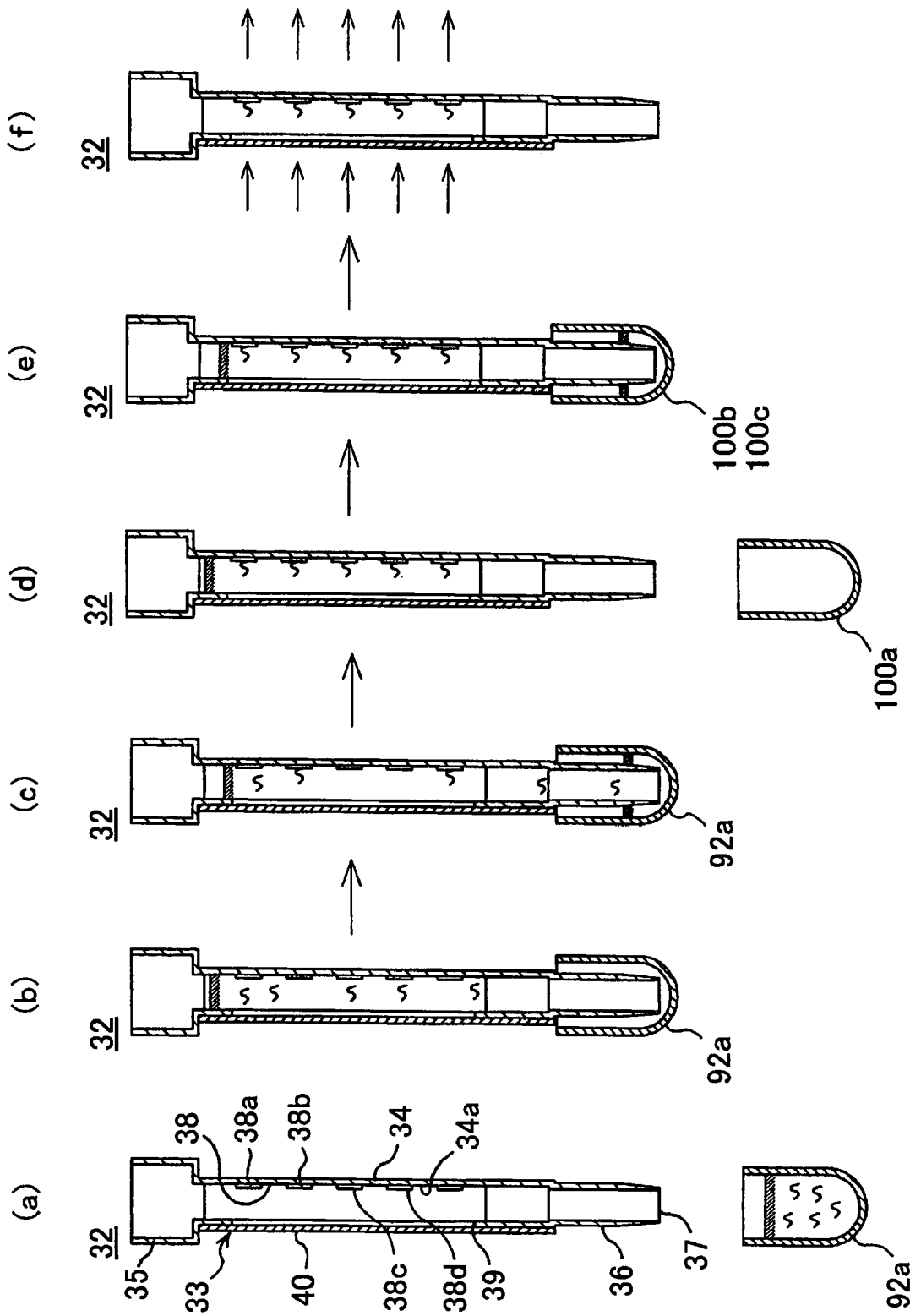
FIG. 9 is a flow diagram showing a biological material fixed region treatment method according to a seventh embodiment.

Next, based on FIG. 9, as DNA processing according to the present embodiment, SNPs (single nucleotide polymorphism) typing is explained for a case where the biological material fixed region enclosing tip 32 is used.

At the plurality of SNP positions that are to be measured, an oligonucleotide, which has a possibility of hybridization, that has a base sequence, is fixed to the fixing region 38 as a probe material. In order to perform fixing to the fixing region 38, a functional group is generated or expressed beforehand at the surface of the fixing region 38, it is bonded with the probe material, and the surface is cleaned with a suitable solvent.

For example, at SNP1 (a first position), there is a possibility of two types, the base T or the base C, and at SNP2 (a second position), there is a possibility of two types, the base G or the base A.

A fixing position 38a of the fixing region 38 fixed with a base sequence for determining the base T at SNP1, a fixing position 38b of the fixing region 38 fixed with a base sequence for determining the base C at SNP1, a fixing position 38c of the fixing region 38 fixed with a base sequence for determining the base G at SNP2, and a fixing position 38d of the fixing region 38 fixed with a base sequence for determining the base A at SNP2 are, as shown in FIG. 9(a), formed on the major side face 34a with the greatest area of the side faces of the fixing region forming section 34 of the tip form vessel 33 which has a translucency. At this time a dispensing mechanism that passes the fluid through the dispensing opening part 39 of the tip form vessel 33 is used to dispense the fluid. On completion of dispensing, the dispensing opening part 39 is covered by the lid member 40 of the enclosing section and thereby sealed. As a result, the biological material fixed region enclosing tip 32 is formed.

For example, in regard to eight test subjects, a case where the SNPs typing position of a respective plurality of positions (two positions in this example) are attempted to be simultaneously determined, is explained. In this case, in a step S1, in regard to a biological material fixed region enclosing tip 32 that is formed in this manner, the nozzle 117 of the biological material fixed region enclosing tip processing device 80 is installed to the installation opening part 35 provided on the upper side of the fixing region forming section 37 thereof.

On the other hand, specimens such as the following are stored in the eight specimen storage wells 92a provided in the tip processing region 81. That is to say, the genome is respectively extracted from the blood of the eight test subjects, and amongst these genomes, the fragments that contain a plurality of positions of the SNPs typing positions are amplified by a thermal cycler, a material that is labeled by a fluorescent material is generated, and this is stored per test subject in the eight specimen wells 92a. Furthermore, in the eight consecutive cartridge vessels 100, a BW buffer solution is stored in the wells 100a to 100c thereof.

In a step S2, as shown in FIG. 9(a), the collective nozzle head 84 of the biological material fixed region enclosing tip processing device 80 is advanced in the row direction by means of the movement device, the narrow tubes 36 are simultaneously inserted into the specimen storage wells 92a, and the insides of the fixing region forming sections 34 are simultaneously filled by performing suction of a suspension that is inside the specimen storage wells 92a.

In a step S3, as shown in FIG. 9(b), the fixing region 38 inside the tip form vessel 33 and the suspension are brought into sufficient contact via the nozzle, for example, by stirring as a result of repeating suction and discharge ten times at a predetermined speed s1 (for example, approximately 200 microliters/sec), and in an amount v1 (for example, approximately 400 microliters).

Then, in a step S4, as shown in FIG. 9(c), the DNA fragments within the suspension, which have been labeled by a fluorescent material, bond to the oligonucleotide at the fixing position of the fixing region 38 amongst the positions of the SNP by means of hybridization. The residual liquid is discharged into the specimen storage well 92a.

In a step S5, as shown in FIG. 9(d), in regard to the biological material fixed region enclosing tip processing device 80, the biological material fixed region enclosing tip 32 that encloses the fixing region 38, for which the reaction has been completed, is transported to the location of the wells 100a of the eight consecutive cartridge vessels 100, and with respect to the BW buffer solution, cleaning is performed by repeating suction and discharge ten times, for example, by means of a predetermined speed s2 (for example, from approximately 760 to 1700 microliters/sec) in a microamount v2 (for example, approximately 500 microliters). Furthermore, as shown in FIG. 9(e), the same operation is repeated with respect to the wells 100b and 100c.

In a step S6, in regard to the biological material fixed region enclosing tip 32, for which cleaning has been completed, the collective nozzle head 84 is moved to the position of the tip storage section 102 that is stopped on the column transporting route 103a of the conveyor 103, separated from the plurality of consecutive nozzles 117 provided to the collective nozzle head 84a by means of the claw 122 and stored in the tip storing section 102, and transported along the transporting route by driving the conveyor 103. At the time the tip storage section 102 reaches the row transporting route 103b, following suction of a predetermined reagent by moving the individual nozzle head 84' to the reagent storage section 77, amongst the eight tip storage sections 102 that are stopped along the row transporting route 103b, dispensing of a reagent for measurement is performed from the installation opening part 35 of the selected biological material fixed region enclosing tip 32, for example, as the predetermined reagent. Thereafter, it is transported to the measurement position 104 provided on the transporting route by driving the conveyor 103. As shown in FIG. 9(f), an excitation light is irradiated at the measurement position 104, and the light within the fixing region forming section 34 is received at the light receiving section 106. By performing measurement of the light emission position, analysis of the structure of the target material is performed.

Figure 10:
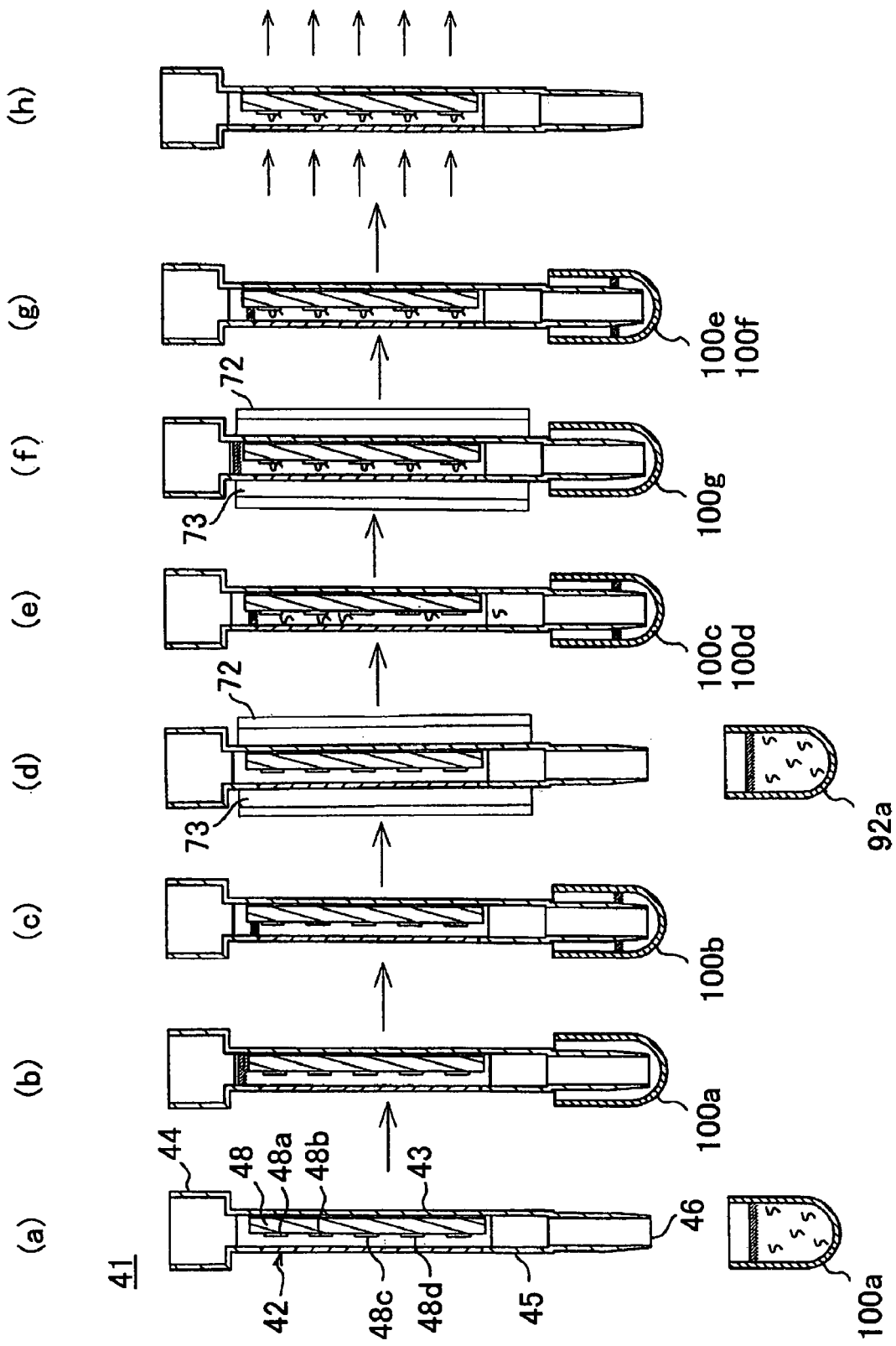
FIG. 10 is a flow diagram showing a biological material fixed region treatment method according to an eighth embodiment.

Next, based on FIG. 10, the processing procedure with respect to an allergy test as a protein analysis example is described for a case where the biological material fixed region enclosing tip 41 is used.

Various allergen materials, for example, materials obtained from cedar pollen, ragweed, mites, mold, or the like, are fixed to the plate-shaped carriers 49 provided with the fixing regions 48. In order to fix the allergen materials to the fixing positions 48a and 48b of the plate-shaped carriers 49, a functional group is generated or expressed beforehand on the surface of the plate-shaped carriers 49. The plate-shaped carrier 49 fixed with these allergen materials, is inserted inside the fixing region forming section 43 which has a translucency by passing through the installation opening part 47. Then after insertion, the lid member 50 is engaged with the engaging section 43b of the fixing region forming section 43, is installed by welding as a result of adhesion, ultrasonic waves or heat, and is enclosed, and the biological material fixed region enclosing tip 41 is formed.

As shown in FIG. 10, in a step S11, in regard to the biological material fixed region enclosing tip 41 obtained in this manner, the nozzle 117 of the biological material fixed region enclosing tip processing device 80 is installed to the installation opening part 44 provided to the upper side of the fixing region forming section 43 thereof.

On the other hand, blood collected from the eight test subjects is stored in the specimen storage wells 92a provided to the tip processing region 81, and in the eight consecutive cartridge vessels 100, a 50 mM TBS buffer solution and a pH 8, 1% BSA solution are stored in the wells 100a, a cleaning solution comprising a 50 mM TBS buffer solution and a pH 8, 0.005% Tween solution are stored in the wells 100b to 100f, and a liquid that suspends an anti-human IgE antibody that has been labeled with a fluorescent material is stored in the wells 100g.

In a step S12, as shown in FIGS. 10(a) and (b), the solutions are stirred by performing suction and discharge of an amount v3 (a volume of the carrier inside the tip filled by liquid; for example, approximately 500 microliters) of the solution stored in the wells 100a at a speed s3 (slow so as not to form bubbles; for example, approximately 760 microliters/sec), and the fixing region 48 of the surface of the plate-shaped carrier 49 is blocked (shutoff).

In a step S13, as shown in FIG. 10(c), cleaning is performed with the 50 mM TBS buffer solution and pH 8, 0.005% Tween solution that is stored in the wells 100b. Furthermore, in a step S14, as shown in FIG. 10(d), the biological material fixed region enclosing tip 41 installed to the nozzle is moved to the specimen storage well 92a, the blood stored in the specimen storage well 92a is suctioned into the tip form vessel 42 and brought into contact, and the IgE antibody in the blood and the allergen material is reacted within the tip form vessel 42 for 30 minutes at 37 degrees. At that time, in order to maintain the tip form vessel 42 interior at a constant temperature, it is heated such that the tip form vessel 42 is sandwiched from both sides and nine heating walls 72 and heating plates 73 of the temperature raising and lowering device 71, which are arranged in a comb form, approach both sides of the eight consecutive biological material fixed region enclosing tip 41. Consequently, the inside of the tip form vessel 42 interior can be efficiently heated with certainty.

Next, in a step S15, as shown in FIG. 10(e), the biological material fixed region enclosing tip 41 is moved to the wells 100c of the cartridge vessel 100. The aforementioned cleaning solution is stored in the wells 100c, and cleaning is performed by repeating suction and discharge ten times at, for example a speed s4 (for example, from approximately 760 microliters to 1700 microliters/sec) and in an amount v4 (for example, approximately 500 microliters). Furthermore, the biological material fixed region enclosing tip 41 is transported to the wells 100d, and cleaning is repeated.

Next, in a step S16, as shown in FIG. 10(f), the collective nozzle head 84 is moved to the wells 100g, the suspension is suctioned and brought into contact with the plate-shaped carrier 49 in order to react with the anti-human IgE antibody stored in the wells 100g, which has been labeled with fluorescent light, and it is maintained at 37° C. for 30 minutes. Also in this case, as mentioned above, the inside of the tip form vessel 43 is heated by approaching the heating wall 72 and the heating plates 72 of the temperature raising and lowering device 71 such that they sandwich both sides of the biological material fixed region enclosing tip 41.

In a step S17, as shown in FIG. 10(g), it is moved to the wells 100e of the cartridge vessel 100, and the fixing region 48 is cleaned by performing suction and discharge of the stored cleaning solution approximately ten times, for example, at a speed s5 (for example, from approximately 760 microliters to 1700 microliters/sec), and in an amount v5 (for example, 500 microliters). The same operation is repeated following movement to the wells 100f.

Next, in a step S18, in regard to the biological material fixed region enclosing tip 41, the collective nozzle head 84 is moved to the tip storage section 102 that is stopped on the column transporting route 103a of the conveyor 103, separated from the plurality of consecutive nozzles 117 provided to the collective nozzle head 84 by means of the claw 122 and stored in the tip storing section 102 that is arranged on the column transporting route 103a, and transported along the transporting route by driving the conveyor 103. At the time the tip storage section 102 reaches the position of the row transporting route 103b, the individual nozzle head 84' is moved to the reagent storage section 77, the predetermined reagent is suctioned, and then amongst the eight tip storage sections 102 that are stopped along the row transporting route 103b, it is moved to the selected biological material fixed region enclosing tip 41, and dispensing of the predetermined reagent is performed from the installation opening part 44 of the selected biological material fixed region enclosing tip 41. Thereafter, at the measurement position 104 provided on the transporting route, as shown in FIG. 10(h), light from the plate-shaped carrier 49 is received and measured at the light receiving section 106, the fluorescence strength of the particle surface is measured, and the reacted allergen material is specified.

Figure 11:
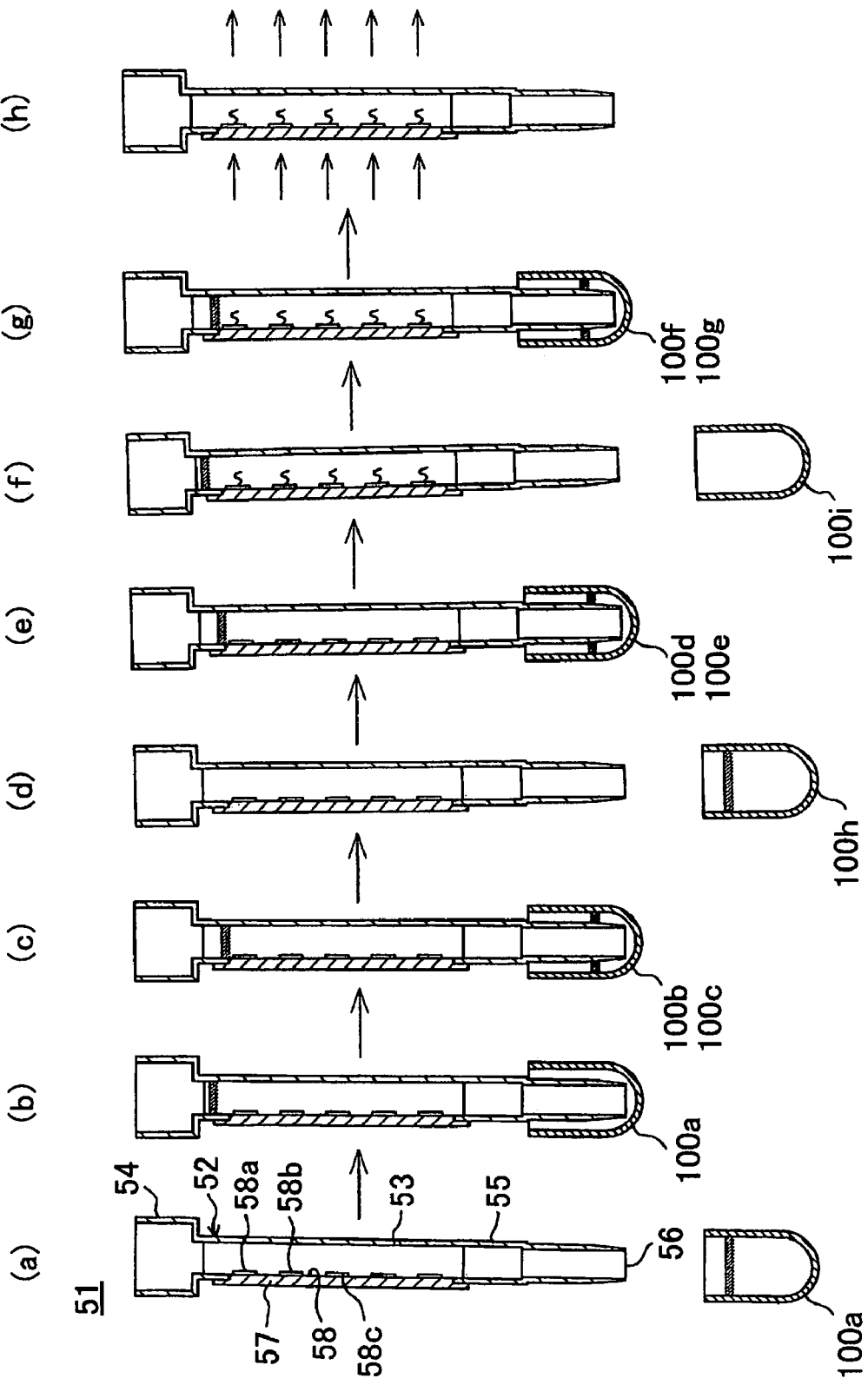
FIG. 11 is a flow diagram showing a biological material fixed region treatment method according to a ninth embodiment.

Next, based on FIG. 11, a protein analysis example using a biological material fixed region enclosing tip 51 with the protein fixed to the fixing region 58, is explained. In the process, in FIG. 11(a), several types (five types in this example) of protein expression base sequences and an oligonucleotide having a protein collection material that collects the expressed proteins are fixed beforehand to the fixing region 58 of the biological material fixed region enclosing tip 51 shown in FIG. 6 with a spacing. In order to fix these materials, a functional group is generated or expressed on the fixing region 58. Consequently, the generated amount of the generated protein, and the bondability with a specific protein are examined. In the present example, the fixing region 58 is formed on one plane face of the plate-shaped carrier 57 formed separate to the tip form vessel 52, and the oligonucleotide is fixed to the predetermined fixing positions. Subsequently, the surface formed with the fixing region 58 of the plate-shaped carrier 57 is faced to the fluid contact opening section 59 side so as to form an inner wall face of the tip form vessel 52 interior, and is fitted to the tip form vessel 52 so as to cover the fluid contact opening section 59, to thereby enclose the fixing region 58, and form the biological material fixed region enclosing tip 51.

On the other hand, within the respective single liquid storage sections 100a of the eight consecutive cartridge vessels 100 provided to the tip processing region 81 of FIG. 7, solutions of amino acids, ribosomes, or the like, are stored, a cleaning solution (hereunder referred to as "PBS-T") comprising a PBS buffer solution and a 0.05% Tween 20 buffer solution, which is a surface active agent is stored in the liquid storage sections 100b to 100g, a 5% skim milk suspension in PBS-T is stored in the liquid storage sections 100h, and a solution of an antibody labeled with a fluorescent material, and a biotinylated material is stored in the liquid storage sections 100i.

In a step S21, in regard to a biological material fixed region enclosing tip 51 that is formed in this manner, the nozzle 117 of the biological material fixed region enclosing tip processing device 80 is installed to the installation opening part 54 provided on the upper side thereof. Next, as shown in FIG. 11(a) and (b), the eight consecutive nozzles 117 of the collective nozzle head 84 of the biological material fixed region enclosing tip processing device 80 are simultaneously moved to the liquid storage section 100a of the cartridge vessels 100, and an amount v6 (for example, approximately 500 microliters) of the solution of the amino acid, or the like, that is stored in the liquid storage sections 100a is suctioned into the tip form vessel 52 at a speed s6 (for example, approximately 760 to 1700 microliters/sec). In this state, the inside of the tip form vessel 52 is heated by flowing an electrical current to the conductive thin film 57a that is formed so as to cover the outside surface of the tip form vessel 57, and it is maintained at 37° C. for 1 hour.

In a step S22, following discharge of the liquid from the narrow tube 51, as shown in FIG. 11(c), the collective nozzle head 84 is moved to the liquid storage sections 100b, and it is washed by repeating suction and discharge of the PBS-T solution with respect to the fixing region forming section 53, for example, ten times, at a speed s7 (for example, from approximately 760 to 1700 microliters/sec), and in an amount v7 (for example, approximately 500 microliters). This operation is also repeated at the liquid storage sections 100c.

In a step S23, as shown in FIG. 11(d), the collective nozzle head 84 is moved to the liquid storage sections 100h, the PBS-T and 5% skim milk suspension is suctioned, then reacted in a room temperature state for approximately 1 hour, and blocking is performed.

In a step S24, following discharge of the liquid from the narrow tube 55, the collective nozzle head 84 is moved to the liquid storage sections 100d, and it is washed by repeating suction and discharge of the PBS-T solution with respect to the narrow tube 55, for example, ten times, at a speed s8 (for example, from approximately 760 to 1700 microliters/sec), and in an amount v8 (for example, approximately 500 microliters). This operation is also repeated at the liquid storage sections 100e.

In a step S25, as shown in FIG. 11(f), the biological material fixed region enclosing tip 51 is transported to the liquid storage sections 100i, and the suspension which suspends an antibody that has been labeled by the fluorescent material, and a biotinylated material, is suctioned, and incubated at room temperature for approximately 30 minutes to 1 hour.

Furthermore, in a step S26, as shown in FIG. 11(g), it is transported to the liquid storage sections 100f, and it is washed by repeating suction and discharge of the PBS-T solution with respect to the narrow tube 55, for example, ten times, at a speed s9 (for example, approximately 760 to 1700 microliters/sec), and in an amount v9 (for example, approximately 500 microliters). This operation is also repeated at the liquid storage sections 100g.

In a step S27, in regard to the biological material fixed region enclosing tip 51, the collective nozzle head 84 is moved to the tip storage section 102 that is stopped on the column transporting route 103a of the conveyor 103, separated from the plurality of consecutive nozzles 117 provided to the collective nozzle head 84 by means of the claw 122 and stored in the tip storing section 102 that is arranged on the column transporting route 103a, and transported along the transporting route by driving the conveyor 103. At the time the tip storage section 102 reaches the row transporting route 103b, the individual nozzle head 84' is moved to the reagent storage section 77, a predetermined reagent is suctioned, and then, amongst the eight tip storage sections 102 that are stopped along the row transporting route 103b, it is moved to the selected biological material fixed region enclosing tip 58, and dispensing of the predetermined reagent is performed from the installation opening part 54 of the biological material fixed region enclosing tip 58. Thereafter, at the measurement position 104 provided on the transporting route, light from the fixing region 58 is received and measured at the light receiving section 106, the fluorescence strength of the particle surface is measured, and the protein that has reacted with the antibody labeled with the fluorescent material, the biotinylated material, or the like, is specified, or the expression amount thereof is measured from the strength and the light emission position thereof.

Figure 12:
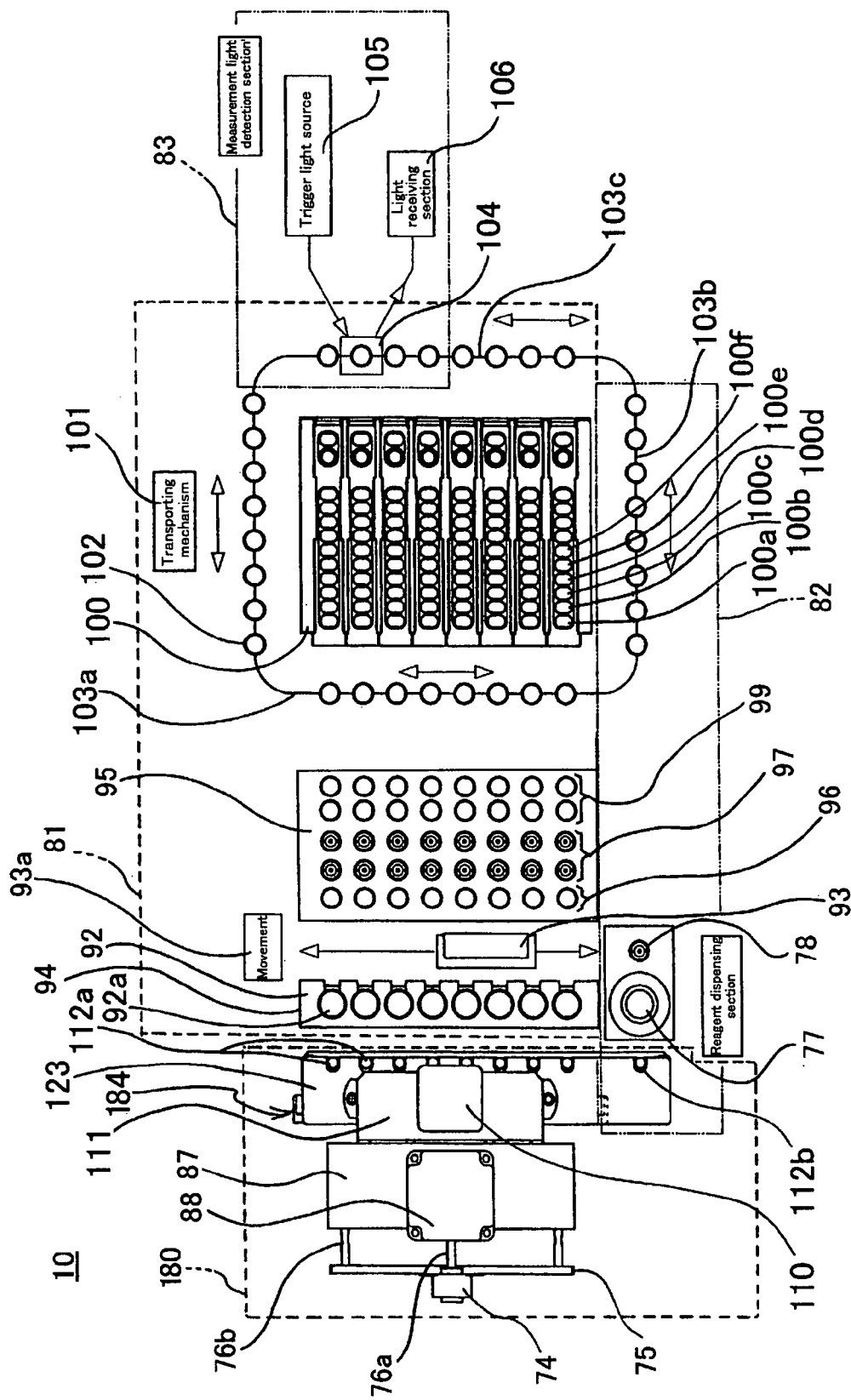
FIG. 12 is a plan view showing an entire biological material fixed region treatment apparatus containing another biological material fixed region enclosing tip treatment apparatus according to the sixth embodiment.

Furthermore it is possible to use a biological material fixed region enclosing tip processing device 180 according to another embodiment shown in FIG. 12 instead of the biological material fixed region enclosing tip processing device 80 shown in FIG. 7 and FIG. 8. In FIG. 12, the same reference symbols as in FIG. 7 and FIG. 8 indicate the same components. The biological material fixed region enclosing tip processing device 180 is one in which suction and discharge of gas is performed using a nozzle that is communicated with a suction and discharge mechanism, although the biological material fixed region enclosing tip processing device 180 has a nozzle head 184 that has a plurality of consecutive (nine consecutive in this example) nozzles 117 that are arranged in the column direction (the vertical direction in the drawing), and with respect to the nozzle head 184, it differs to the nozzle head 84 in that suction and discharge is simultaneously performed by the same suction and discharge mechanism. Amongst the nine consecutive nozzles 117, one nozzle 117 of the end is an individual nozzle, and as shown by the position thereof (the position of reference symbol 112b in FIG. 12), it is provided such that it is somewhat separated from the eight consecutive nozzles 117, that is to say, the position of the collective nozzle (the position of reference symbol 112a in FIG. 12).

In regard to the suction and discharge mechanism, it has a wide diameter section 116 provided to a somewhat upper section of the nozzles 117, and a rod 112 for sliding a plunger 115a within a cylinder 115 that is joined to the nozzles 117. Furthermore, the nine rods 112 are installed such that they sit on eight consecutive end sections 112a and a single end section 112b, that have a larger diameter than the rods 112 and protrude in the radial direction from the eight respective notch sections that are provided to the edge of a driving plate 123, in which simultaneous vertical movement is possible. Hence, the nozzle head 184 simultaneously moves in the row direction (the horizontal direction or the left and right directions on the drawing).

Amongst the nine consecutive nozzles 117, the individual nozzle is provided to the nozzle head 184. Hence the suction and discharge is simultaneously performed together with the other eight consecutive collective nozzles. Furthermore, also in regard to the raising and lowering mechanism, it is simultaneously performed with respect to horizontal movement in the row direction (the left and right directions in FIG. 12). However, the individual nozzle is, in the reagent dispensing region 82, used for dispensing reagents for measurement into the biological material fixed region enclosing tip 11. In a case where the individual nozzle is used, it is in a state where the biological material fixed region enclosing tip has been removed from the other collective nozzles. Furthermore, in a case where the collective nozzles are used, it is in a state where the tip form vessel, or the like, is not installed to the individual nozzle.

The embodiments above have been specifically explained in order to better understand the present invention, and do not restrict other embodiments in any way. Accordingly, they are changeable within a scope that does not depart from the gist of the invention. For example, in the embodiments, although only the cases of DNA and proteins were explained, it may also be a sugar chain, other DNA materials, RNA, or the like. Furthermore, as the fixing region, although only the case where this is provided on one plane face was explained, the fixing region may also be one which is provided on a curved surface, or on two plane faces or on the faces of a solid body. Furthermore, in regard to the numerical values, the frequencies, the shapes, the numbers, the quantities, or the like, that were used in the explanations above, they are not restricted to these cases in any way.

Moreover, in the present invention, as the fixing region, it is also possible to use one where a narrow and long member, such as a thread form, with a flexibility, or a thread form, in which one or more types of biological materials, such as a ligand, are provided such that they are fixed or are fixable, is wound around a carrier. In short, it can be used as the carrier as long as it is one where suction and discharge of fluid can be performed in a state where it is maintained within the fixing region forming section.

Furthermore, by suppressing the chemical material containing the ligand, or the like, with respect to all side faces of the narrow and long member to a low concentration, production is simplified and the reliability thereof is increased, and on the other hand, at the time of processing, by storing the integrated narrow and long member, the processing efficiency can be increased. Furthermore, since at the time of measurement the arrangement of chemical materials can be handled with certainty along a one-dimensional route, the reliability of measurement is high. An example of a narrow and long member with flexibility includes, for example, those that are formed by chemical fibers, such as nylon.

Moreover, the configuration elements above, such as the fixing region, the carriers, the narrow tubes, the nozzle head, the tip form vessel, the sealing section, and the nozzle, as well as the fixing region forming section, the temperature raising and lowering device or the like, and the devices, can be arbitrarily combined while making suitable changes. Furthermore, the ligand is not restricted to DNA, and it includes genetic material such as oligonucleotides and RNA, immunity materials, sugar chains, and further includes pheromones, allomones, mitochondria, viruses, and plasmids.

Furthermore, the aforementioned reagents and materials show examples, and it is also possible to utilize other reagents and materials. Moreover, a carrier in which DNA, or the like, has been collected can be taken out from the narrow tube, or the like, and it can be made the subject of preservation, or other processes.

INDUSTRIAL APPLICABILITY

The present invention relates to a biological material fixed region enclosing tip, a biological material fixed region treatment apparatus and a method thereof. The present invention relates to all fields, such as fields in which handling of biopolymers, such as genes, the immune system, amino acids, proteins, and sugars, and biological low molecular weight compounds is demanded, for example, in agricultural fields such as engineering fields, food products, agricultural produce and seafood processing, medical fields such as pharmacology fields, sanitation, immunity, diseases, and genetics, and science fields such as chemistry or biology. The present invention is, in particular, an effective method in cases where a series of processes using a plurality of reagents and materials is continuously executed in a predetermined order.

BRIEF DESCRIPTION OF THE REFERENCE SYMBOLS

10 Biological material fixed region treatment apparatus
11, 22, 32, 41, 51 Biological material fixed region enclosing tip
12, 23, 33, 42, 52 Tip form vessel
13, 24, 34, 43, 53 Fixing region forming section
17, 48, 58 Fixing region
18, 49, 57 Plate-shaped carrier
18a Annular attachment section (enclosing section)
30, 40, 50 Lid member (enclosing section)
84 Collective nozzle head
84' Individual nozzle head
103 Conveyor (queued route transporting device)
106 Light receiving section
184 Nozzle head

The invention claimed is:
1. A biological material fixed region treatment apparatus comprising:
a nozzle head that has one or a plurality of consecutive nozzles that perform suction and discharge of gas;
a suction and discharge mechanism that performs the suction and discharge of the gas via the nozzles;

one or two or more biological material fixed region enclosing tips, each biological material fixed region enclosing tip comprising:
an upper end;
a lower end;
an installation opening part that is installed or is installable to said nozzles, the installation opening part being provided on the upper end;
an opening through which inflow and outflow of fluid is possible by means of the suction and discharge of the gas, the opening being provided on the lower end; and
a tip form vessel extending between the opening and the installation part opening, the tip form vessel comprising:
a narrow tube that is provided with said opening in the lower end, and is formed narrower than said installation opening part, and so that it is insertable into various vessels;
a wide tube which has translucence, the wide tube being wider than the narrow tube and extending between said narrow tube and said installation opening part, the wide tube defining an internal cavity;
a fixing region positioned internally within the internal cavity of the wide tube, wherein predetermined biological material is fixed in the fixing region and thus in the wide tube in a plurality of different positions that are determined beforehand that are distinguishable from the exterior, which enables analysis of target biological material by measuring light emitted at said positions provided inside said tip form vessel; and
an enclosing section that encloses the fixing region internally within the internal cavity of the wide tube so that the predetermined biological material is able to make contact in an immovable state with the fluid when the fluid is flowing into the wide tube from the opening;
a liquid storage section group, in which a variety of liquids are stored or are storable; and
a movement device that relatively moves said nozzle head with respect to said liquid storage section group;
wherein the suction and discharge of the gas is controlled by controlling the amount, the speed, the frequency, the time, or the position of the suction and discharge of said nozzles, and wherein the control of the suction and discharge of the gas is based on; the structure of said biological material fixed region enclosing tip, material conditions comprising the type of biological material that is fixed in the fixing region or is present within the fluid, the concentration, the amount of liquid, and the coordinate position containing the storage position of the liquid, and processing contents.

2. A biological material fixed region treatment apparatus according to claim 1, further comprising a light reception device that receives light from said fixing region stored within said tip form vessel.

3. A biological material fixed region treatment apparatus according to claim 1, wherein a space in which liquid is storable within said tip form vessel, is several microliters to several hundred microliters.

4. A biological material fixed region treatment apparatus according to claim 1, wherein a temperature raising and lowering body that raises and lowers the temperature as a result of a signal from the exterior is provided in the vicinity of, making contact with, or able to be in the vicinity of or making contact with, the outside of said tip form vessel of said biological material fixed region enclosing tip.

5. A biological material fixed region treatment apparatus according to claim 1, wherein said nozzle head has a plurality of consecutive nozzles arranged along the column direction, and an individual nozzle head that has at least one nozzle, said suction and discharge mechanism simultaneously performs the suction and discharge of the gas with respect to the plurality of consecutive nozzles, and said movement device has, a nozzle head movement device that relatively moves said nozzle head in a row direction with respect to said liquid storage section group, and a transporting route that includes a column transporting route that is on the movement route of said nozzle head and along said column direction and a row transporting route that is on the movement route of said individual nozzle head and along said row direction, and has a queued route transporting device that transports a transport storage section, in which tips that have been detached from said nozzle head or liquid that has been discharged from said nozzle head are respectively storable, along said transporting route.

6. A biological material fixed region treatment apparatus according to claim 1, wherein said nozzle head has a plurality of consecutive nozzles arranged along the column direction, and an individual nozzle head that has at least one nozzle, said suction and discharge mechanism simultaneously performs the suction and discharge of the gas with respect to the plurality of consecutive nozzles and the nozzle of said individual nozzle head, and said movement device has, a nozzle head movement device that relatively moves said nozzle head along a row direction with respect to said liquid storage section group, and a transporting route that includes a column transporting route that is on the movement route of said plurality of consecutive nozzles and along said column direction and a row transporting route that is on the movement route of said nozzle of the individual nozzle head and along said row direction, and has a queued route transporting device that transports a transport storage section, in which tip form vessels that have been detached from said plurality of consecutive nozzles or liquid that has been discharged from said nozzle head are respectively storable, along said transporting route.

7. A biological material fixed region treatment apparatus according to claim 5, wherein a light reception device, which receives light from said transport storage section, is provided at a predetermined position along said transporting route of said queued route transporting device.

8. A biological material fixed region treatment apparatus according to claim 2, wherein the tip form vessel further comprises a plate-shaped carrier that is wider than the narrow tube; wherein the fixing region is formed on the plate-shaped carrier and the plate-shaped carrier extends, relative to the wide tube, so that the predetermined biological material is fixed on the plate-shaped carrier within the wide tube.

9. A biological material fixed region treatment apparatus according to claim 8, wherein the enclosing section comprises one of the following:

an annular attachment member engaged with an inside wall of the upper end and attached to the plate-shaped carrier;

a plate-shaped lid member attached to the wide tube, the plate-shaped lid member closing an opening section formed in the wide tube, the plate-shaped lid member being spaced from the plate-shaped carrier in a parallel relation; and the plate-shaped carrier, the plate-shaped carrier being attached to the wide tube, the plate-shaped carrier closing an opening section formed in the wide tube, the plate-shaped carrier defining an inside wall of the wide tube on which the fixing region is formed.

\* \* \* \* \*